US010159654B2

(12) United States Patent
Antony

(10) Patent No.: US 10,159,654 B2
(45) Date of Patent: Dec. 25, 2018

(54) FORMULATION OF CURCUMIN WITH ENHANCED BIOAVAILABILITY OF CURCUMIN AND METHOD OF PREPARATION AND TREATMENT THEREOF

(71) Applicant: Arjuna Natural Extracts, Ltd., Alwaye (IN)

(72) Inventor: Benny Antony, Ankamaly (IN)

(73) Assignee: ARJUNA NATURAL EXTRACTS, LTD, Alwaye (IN)

(*) Notice: Subject to any disclaimer, the term of this patent is extended or adjusted under 35 U.S.C. 154(b) by 149 days.

(21) Appl. No.: 14/476,555

(22) Filed: Sep. 3, 2014

(65) Prior Publication Data
US 2014/0371327 A1 Dec. 18, 2014

Related U.S. Application Data

(60) Division of application No. 13/645,031, filed on Oct. 4, 2012, now Pat. No. 8,859,020, and a continuation-in-part of application No. 14/094,725, filed on Dec. 2, 2013, now Pat. No. 8,895,087, and a continuation-in-part of application No. 13/674,249, filed on Nov. 12, 2012, now Pat. No. 8,993,013, said application No. 13/645,031 is a continuation-in-part of application No. PCT/IN2011/000232, filed on Apr. 4, 2011, and a continuation-in-part of application No. 13/385,717, filed on Mar. 5, 2012, now Pat. No. 8,623,431, and a continuation-in-part of application No. 13/506,572, filed on Apr. 30, 2012, now Pat. No. 8,329,233, said application No. 14/094,725 is a division of application No. 13/385,717, filed on Mar. 5, 2012, now Pat. No. 8,623,431, which is a division of application No. 12/926,985, filed on Dec. 21, 2010, now Pat. No. 8,153,172, which is a division of application No. 12/662,740, filed on Apr. 30, 2010, now Pat. No. 7,879,373, which is a division of application No. 11/635,599, filed on Dec. 8, 2006, now Pat. No. 7,736,679, said application No. 13/674,249 is a division of application No. 13/506,572, filed on Apr. 30, 2012, now Pat. No. 8,329,233, which is a division of application No. 12/926,980, filed on Dec. 21, 2010, now Pat. No. 8,197,869, which is a division of application No. 12/073,864, filed on Mar. 11, 2008, now Pat. No. 7,883,728, which is a continuation-in-part of application No. 11/635,599, filed on Dec. 8, 2006, now Pat. No. 7,736,679, which is a continuation of application No. PCT/IN2005/000176, filed on May 30, 2005.

(30) Foreign Application Priority Data

Apr. 5, 2010 (IN) .............. 950CHE2010

(51) Int. Cl.
A61K 31/12 (2006.01)
A61K 36/9066 (2006.01)

(52) U.S. Cl.
CPC .......... A61K 31/12 (2013.01); A61K 36/9066 (2013.01)

(58) Field of Classification Search
None
See application file for complete search history.

(56) References Cited

U.S. PATENT DOCUMENTS

| 3,340,250 | A | 9/1967 | Sair |
| 5,536,506 | A | 7/1996 | Majeed |
| 5,861,415 | A | 1/1999 | Majeed |
| 6,224,871 | B1 | 5/2001 | Hastings |
| 6,224,877 | B1 | 5/2001 | Gaikar |
| 6,235,287 | B1 | 5/2001 | Weidner |
| 6,245,350 | B1 | 6/2001 | Amey |
| 6,344,475 | B1 | 2/2002 | Caplan |
| 6,576,273 | B2 | 6/2003 | Madsen |
| 6,827,951 | B2 | 12/2004 | Newmark |
| 6,942,881 | B2 | 9/2005 | Madsen |

(Continued)

FOREIGN PATENT DOCUMENTS

| CN | 1489994 A | * | 4/2004 |
| CN | 1548121 A | | 11/2004 |

(Continued)

OTHER PUBLICATIONS

Aratanechemuge, Y, Komiya, T, Moteki H, Katsuzaki, H, Imai, K, and Hibasami, H, Selective Induction of Apoptosis by ar-Turmerone Isolated From Turmeric (Curcuma longa L) In Two Human Leukemia Cell Lines, But Not in Human Stomach Cancer Cell Line, International Journal of Molecular Medicine, 9:481-484 (2002).

Jayaprakasha, GK, Jena, BS, Negi, PS, and Sakariah, KK, Evaluation of Antioxidant Activities and Aminmutagenicity of Turmeric Oil: A Byproduct from Curcumin Production, Biosciences, 57(9/10):828-835 (2002).

Kelloff, GJ, Crowell, JA, Hawk ET, Steele, VE, Lubet, RA, Boone, CW, Covey JM, Doody, LA, Omenn, GS, Greenwald, P, Hong, WK, Parkinson, DR, Bagheri, D, Baxter, GT, Blunden, M, Doeltz, MK, Eisenhauer KM, Johnson, K, Knapp, GG, Longfellow, DG, Malone, WF, Nayfield, SG, Seifried, HE, Swall, LM, and Sigman, CC, Strategy and Planning for Chemopreventive Drug Development: Clinical Development Plans II, Journal of Cellular Biochemistry, 268:54-71 (1996).

(Continued)

Primary Examiner — Amy L Clark
(74) Attorney, Agent, or Firm — Jyoti C. Iyer

(57) ABSTRACT

Disclosure provides a formulation of curcuminoid with essential oil of turmeric to enhance the bioavailability of curcumin and to augment the biological activity of curcumin, wherein curcumin is the main constituent of curcuminoid and wherein Ar-turmerone is the main constituent of the essential oil of turmeric. An application of curcuminoid with essential oil of turmeric to enhance the bioavailability of curcumin for oral supplementation against a variety of diseases and method of doing the same is provided.

26 Claims, 9 Drawing Sheets

(56) References Cited

U.S. PATENT DOCUMENTS

| | | | |
|---|---|---|---|
| 6,982,099 B2 | 1/2006 | Newmark | |
| 6,991,814 B2 | 1/2006 | Ray | |
| 7,037,524 B2 | 5/2006 | Gow | |
| 7,041,321 B2 | 5/2006 | Newmark | |
| 7,067,159 B2 | 6/2006 | Newmark | |
| 7,070,816 B2 | 7/2006 | Newmark | |
| 7,736,679 B2* | 6/2010 | Antony | A61K 36/9066 424/756 |
| 7,879,373 B2* | 2/2011 | Antony | A61K 36/9066 424/756 |
| 7,883,728 B2* | 2/2011 | Antony | A61K 36/9066 424/756 |
| 8,153,172 B2* | 4/2012 | Antony | A61K 36/9066 424/756 |
| 8,197,869 B2* | 6/2012 | Antony | A61K 36/9066 424/756 |
| 8,329,233 B2* | 12/2012 | Antony | A61K 36/9066 424/756 |
| 8,623,431 B2* | 1/2014 | Antony | A61K 36/9066 424/756 |
| 8,859,020 B2* | 10/2014 | Antony | A61K 36/9066 424/725 |
| 8,895,087 B2* | 11/2014 | Antony | A61K 36/9066 424/756 |
| 8,993,013 B2* | 3/2015 | Antony | A61K 36/9066 424/756 |
| 2002/0136786 A1 | 9/2002 | Newmark | |
| 2004/0247664 A1 | 12/2004 | Dreja | |
| 2005/0123632 A1 | 6/2005 | Chen | |
| 2006/0051438 A1 | 3/2006 | Ray | |
| 2007/0148263 A1* | 6/2007 | Antony | A61K 36/9066 424/756 |
| 2008/0226755 A1* | 9/2008 | Antony | A61K 36/9066 424/725 |
| 2010/0217045 A1* | 8/2010 | Antony | A61K 36/9066 568/309 |
| 2011/0092603 A1* | 4/2011 | Antony | A61K 36/9066 514/679 |
| 2011/0098361 A1* | 4/2011 | Antony | A61K 36/9066 514/679 |
| 2012/0207863 A1* | 8/2012 | Antony | A61K 36/9066 424/756 |
| 2012/0220666 A1* | 8/2012 | Antony | A61K 36/9066 514/679 |
| 2014/0088200 A1* | 3/2014 | Antony | A61K 36/9066 514/679 |
| 2014/0093594 A1* | 4/2014 | Antony | A61K 36/9066 424/756 |
| 2014/0099390 A1* | 4/2014 | Antony | A61K 36/9066 424/756 |
| 2014/0193533 A1* | 7/2014 | Antony | A61K 31/12 424/756 |
| 2014/0295005 A9* | 10/2014 | Antony | A61K 36/9066 424/756 |
| 2014/0371327 A1* | 12/2014 | Antony | A61K 36/9066 514/679 |
| 2015/0037442 A1* | 2/2015 | Antony | A61K 36/9066 424/756 |
| 2015/0157718 A1* | 6/2015 | Antony | A61K 36/9066 514/679 |
| 2016/0008479 A1* | 1/2016 | Antony | A61K 47/46 514/679 |
| 2016/0067300 A1* | 3/2016 | Antony | A61K 36/9066 424/400 |

FOREIGN PATENT DOCUMENTS

| | | |
|---|---|---|
| EP | 1465646 A1 | 10/2004 |
| IN | 457/RQ/CHE/2003 | 7/2005 |
| IN | 200430 | 5/2006 |
| JP | 2000-228966 A | 8/2000 |
| JP | 2004524304 A | 8/2004 |
| JP | 2004331539 A | 11/2004 |
| WO | WO 02074295 A1 | 9/2002 |
| WO | WO 03/049753 A1 | 6/2003 |
| WO | WO 03/075685 A1 | 9/2003 |

OTHER PUBLICATIONS

Rao, CV, Rivenson, A, Simi, B, and Reddy, BS, Chemopreventive of Colon Carcinogenesis by Dietary Curcumin, a Naturally Occurring Plant Phenolic Compound, Cancer Research, 55:259-266 (1995).

Subramanian, M, Sreejayan, Rao, MNA, Devasagayam, TPA, and Singh, BB, Diminution of Singlet Oxygen-Induced DNA Damage by Curcumin and Related Antioxidants, Mutation Research, 311-249-255 (1994).

Tennesen, HH, and Greenhill, JV, Studies on Curcumin and Curcuminoids, XXII: Curcumin as a Reducing Agent and as a Radical Scavenger, International Journal of Pharmaceutics, 87:79-87 (1992).

Reddy, ACP, and Lokesh, BR, Studies on the Inhibtory Effects of Curcumin and Eugenol on the Formation of Reactive Oxygen Species and the Oxidation of Ferrous Iron, Molecular and Cellular Biochemistry, 137:1-8 (1994).

Donatus, IA, Sardjoko, and Vermeulen, NPE, Cytotoxic and Cytoprotective Activities of Curcumin, Biochemical Pharmacology, 39(12):1869-1875 (1990).

Sharma, SC, Mukhtar, H, Sharma, SK, Murti, CRK, Lipid Peroxide Formation in Experimental Inflammation, Biochemical Pharmacology, 21:1210-1214 (1972).

Liu, J-Y, Lin, S-J, and Lin, J-K, Inhibitory Effects of Curcumin on Protein Kinase C Activity Induced by 12-O-tetradecanoyl-Phorbol-13-Acetate in NIH 3T3 Cells, Carcinogenesis, 14(5):857-861 (1993).

Huang, T-S, Lee, S-C, and Lin, J-K, Suppression of c-Jun/ AP-1 Activation by an inhibitor of Tumor Promotion in Mouse Fibroblast Cells, Proc. Natl. Acad. Sci. U.S.A. 88:5292-5296 (1991).

Huang, M-T, Lysz, T,Ferraro, T, and Conney, AH, Inhibitory Effects of Curcumin on Tumor Promotion and Arachidonic Acid Metabolism in Mouse Epidermis, Cancer Chemoprevention, pp. 375-391 (1992), CRC Press, Inc.

Huang, M-T, Lysz, T, Ferraro, T, Abidi, TF, Laskin, JD, and Conney, AH, Inhibitory Effects of Curcumin on In Vitro Lipoxygenase and Cyclooxygenase Activities in Mouse Epidermis, Cancer Research, 51:813-819 (1991).

Plummer, SM, Holloway, KA, Manson, MM, Munks, RJL, Kaptein, A, Farrow, S, and Howells, L, Inhibition of Cyclo-Oxygenase 2 Expression in Colon Cells by the Chemopreventive Agent Curcumin Involves Inhibition of NF-KB Activation Via the NIK/IKK Signalling Complex, Oncogene, 18:6013-6020 (1999).

Funk, CD, Funk, LB, Kennedy, ME, Pong, AS, and Fitzgerald, GA, Human Platelet / Erythroleukemia Cell Prostaglandin G/H Synthase: cDNA Cloning, Expression, and Gene Chromosomal Assignment, FASEB Journal, 5:2304-2312 (1991).

Subbaramaiah, K, Telang, N, Ramonetti, JT, Araki, R, Devito, B, Weksler, BB, and Dannenberg, AJ, Transcription of Cyclooxygenase-2 is Enhanced in Transformed Mammary Epithelial Cells, Cancer Research, 56:4424-4429 (1996).

Dubois, RN, Awad, J, Morrow, J, Roberts, LJ, and Bishop, PR, Regulation of Eicosanoid Production and Mitogenesis in Rat Intestinal Epithelial Cells by Transforming Growth Factor -α and Phorbol Ester, J. Clin. Invest., 93:493-498 (1994).

Kelley, DJ, Mestre, JR, Subbaramaiah, K, Sacks, PG, Schantz, SP, Tanabe, T, Inoue, H, Ramonetti, JT, and Dannenberg, AJ, Benzo[α]pyrene Up-Regulates Cyclooxygenase-2 Gene Expression in Oral Epithelial Cells, Carcinogenesis, 18(4):795-799 (1997).

Huang, M-T, Smart, RC, Wong, C-Q, and Conney, AH, Inhibitory Effect of Curcumin, Chlorogenic Acid, Caffeic Acid, and Ferulic Acid on Tumor Promotion in Mouse Skin by 12-O-Tetradecanoylphorbol-13-Acetate, Cancer Research, 48:5941-5946 (1988).

Asai, A and Miyazawa, T, Occurrence of Orally Administered Curcuminoid as Glucuronide and Glucuronide/Sulfate Conjugates in Rat Plasma, Life Sciences, 67:2785-2793 (2000).

(56) References Cited

OTHER PUBLICATIONS

Ravindranath, V, and Chandrasekhara, N, In Vitro Studies on the Intestinal Absorption of Curcumin in Rats, Toxicology, 20:251-257 (1981).
Limtrakul, P, Lipigorngoson, S, Namwong, O, Apisariyakui, A, and Dunn, FW, Inhibitory Effect of Dietary Curcumin on Skin Carcinogenesis in Mice, Cancer Letters, 116:197-203 (1997).
Inano, H, and Onoda, M, Prevention of Radiation-Induced Mammary Tumors, Int. J. Radiation Oncology Biol. Phys, 52(1):212-223 (2002).
Inano, H, and Onoda, M, Radioprotective Action of Curcumin Extracted From *Curcuma longa* Linn: Inhibitory Effect on Formation of Urinary 8-Hydroxy-2-Deoxyguanosine, Tumorigenesis, But Not Mortality, Induced by γRay Irradiation, Int. J. Radiation Oncology Biol. Phys., 53(3):735-743 (2002).
Shoba, G, Joy, D, Joseph, T, Majeed, M, Rajendran, R, and Srinivas, PSSR, Influence of Piperine on the Pharmacokinetics of Curcumin in Animals and Human Volunteers, Planta Medica, 64:353-356 (1998).
Began, G, Sudharshan, E, Sankar, KU, and Rao, AGA, Interaction of Curcumin With Phosphatidylcholine: A Spectrofluorometric Study, J. Agric. Food Chem, 47:4992-4997 (1999).
Lantz, RC, Chen, GJ, Solyom, AM, Jolad, SD, and Timmermann, BN, The Effect of Tumeric Extracts on Inflammatory Mediator Production, Phytomedicine 12:445-452 (2005).
Nishiyama, T, Mae, T, Kishida, H, Tsukagawa, M, Mimaki, Y, Kuroda, M, Sashida, Y, Takahashi, K, Kawada, T, Nakagawa, K, and Kitahara, M. Curcuminoids and Sesquiterpenoids in Turmeric (Curcuma longa L) Supress an Increase in Blood Glucose Level in Type 2 Diabetic KK-A$^y$mice, J. Agric. Food Chem, 53-959-963 (2005).
Li, L, Braiteh, FS, and Kurzrock, R, Liposome-Encapsulated Curcumin, In Vitro and In Vivo *Effects on Proliferation, Apoptosis, Signaling, and Angiogenesis*, Cancer, 104(6):1322-1331 (2005).
Kumar, V, Lewis, SA, Mutalik, S, Shenoy, DB, Venkatesh and Udupa, N, Biodegradable Microspheres of Curcumin for Treatment of Inflammation, Indian J Physical Pharmacol, 46(2): 209-217 (2002).
Ammon, HPT, and Wahl, MA, Pharmacology of *Curcuma Longa*, Planta Med. 57:1-7, (1991).
Ravindranath, V, and Chandrasekhara, N, Absorption and Tissue Distribution of Curcumin in Rats, Toxicology, 16: 259-265 (1980).
Wahlstrom, B, and Blennow, G, A Study on the Fate of Curcumin in the Rat, Acta Pharmaol. et Toxicol., 43:86-92 (1978).
Monograph, *Curcuma longa* (Turmeric), Alternative Medicine Review, vol. 6 (Supplement): S62-S66 (2001).
Piyachaturawat, P, Glinsukon, T, and Toskulkao, C, Acute and Subacute Toxicity of Piperine in Mice, Rats and Hamsters, Toxicology Letters, 16:351-359 (1983).
Matsuo, T, Toyota, A, Kanamori, H, Nakamura, K, Katsuki, S, Sekita, S, and Satake, M, Constituents of Representative Curcuma and Estimation of Curcuma Species in Health Foods, Bulletin of the Hiroshima Prefectural Institute of Public Health and Environment, 10:7-13 (2002), Japan Science and Technology Agency.
Kawamori, T, Lubei, R, Steele, VE, Kelloff, GJ, Kaskey, RB, RAO, CV, and Reddy, BS, Chemopreventive Effect of Curcumin, A Naturally Occuring Anti-Inflammatory Agent, During the Promotion/Progression Stages of Colon Cancer, Cancer Res., 59:597-601 (1999), American Association for Cancer Research.
Mahmoud, NN, Carothers, AM, Grunberger, D, Bilinski, RT, Churchill, MR, Martucci, C, Newmark, HL, and Bertagnolli, MM, Plant Phenolics Decrease Intestinal Tumors in an Animal Model of Familial Adenomatous Polyposis, Carcinogenesis, 21(5):921-927 (2000), Oxford University Press.
Zhang, F, Altorki, NK, Mestre, JR, Subbaramaiah, K, and Dannenberg, AJ, Curcumin Inhibits Cyclooxygenase-2 transcription in Bile Acid- and Phorbol Ester-Treated Human Gastrointestinal Epithelial Cells, Carcinogenesis, 20(3): 445-451 (1999), Oxford University Press.
Ireson, C, Orr, S, Jones, DJL, Verschoyle, R, Lim, C-K, Luo, J-L, Howells, I., Plummer, S, Jukes, R. Williams, M, Steward, WP, and Gescher, A, Characterization of Metabolites of the Chemopreventive Agent Curcumin in Human and Rat Hepatocytes and in the Rat in Vivo, and Evaluation of Their Ability to Inhibit Phorbol Ester-Induced Prostaglandin $E_2$ Production, Cancer Res., 61:1058-1064 (2001), American Association for Cancer Research.
Sharma, RA, McLelland, HR, Hill, KA, Ireson CR, Euden, SA, Manson NM, Pirmohamed, M, Marnet, LJ, Gescher, AJ, and Steward, WP, Pharmacodynamic and Pharmacokinetic Study of Oral Curcuma Extract in Patients with Colorectal Cancer, Clin. Cancer Res., 7:1894-1900 (2001), American Association for Cancer Research.
Pan, M-H, Huang, T-M, and Lin, J-K, Biotransformation of Curcumin Through Reduction and Glucoronidation in Mice, Drug Metabolism and Disposition, 27(1):486-494 (1999), American Society for Pharmacology and Experimental Therapeutics.
Ireson, CR, Jones, DJL, Orr, S, Coughtrie, MWH, Boocock, DJ, Williams ML., Farmer, PB, Steward, WP, and Gescher, AJ, Metabolism of the Cancer Chemopreventive Agent Curcumin in Human and Rat Intestine, Cancer Epidemiology, Biomarkers & Prevention, 11:105-111 (2002), American Association for Cancer Research.
Perkins, S, Verschoyle, Rd, Hill, K, Parven, I, Threadgill, MD, Sharma, RA, Williams, ML, Steward, WP, and Gescher, AJ, Chemopreventive Efficacy and Pharmacokinetics of Curcumin in the Min/+ Mouse, A Model of Familial Adenomatous Polyposis, Cancer Epidemiology, Biomarkers & Prevention, 11:535-540 (2002), American Association for Cancer Research.
Chuang, SE, Kuo, MI, HSU, CH, Chen, CR, Lin, JK, Lai, GM, Hsieh, CY, and Cheng, AL, Curcumin-Containing Diet Inhibits Diethylnitrosamine-Induced Murine Hepatocarcinogenesis, Carcinogenesis, 21(2):331-335 (2000), Oxford University Press.
Inano, H, Onoda, M, Inafuku, N, Kubota, M, Kamada, Y, Osawa, T, Kobayashi, H, and Wakabayashi, K, Patent Preventive Action of Curcumin on Radiation-Induced Initiation of Mammary Tumorigenesis in Rats, Carcinogenesis, 21(10):1835-1841 (2000), Oxford University Press.
Garcea, G, Berry, DP, Jones, DJL, Singh, R, Dennison, AR, Farmer, PB, Sharma, RA, Steward, WP, and Gescher, AJ, Consumption of the Putative Chemopreventive Agent Curcumin by Cancer Patients: Assessment of Curcumin Levels in the Colorectum and their Pharmacodynamic Consequences, Cancer Epidemiology, Biomarkers & Prevention, 14(1) 120-125 (2005), American Association for Cancer Research.
Govindarajan, VS and Stahl, WH, Turmeric—Chemistry, technology, and Quality, CRC Critical Reviews in Food Science and Nutrition, 12(3):199-301 (1980).
Sharma RA, Ireson, CR, Verschoyle, RD, Hill, KA, Williams, MI, Leuratti, C, Manson, MM, Marnett, LJ, Steward, WP, and Gescher, A, Effects of Dietary Curcumin on Glutathione S-Transferase and Malondialdehyde-DNA Adducts in Rat Liver and Colon Mucosa: Relationship with Drug Levels, Clinical Cancer Research, 7:1452-1458 (2001).
Sharma, RA, Euden, SA, Platton, SL, Cooke, DN, Shafayat, A, Hewitt, HR, Marczylo, TH, Morgan, B, Hemigway, D, Plummer, SM, Pirmohamed, M, Gescher, AJ and Steward, WP, Phase 1 Clinical Trial of Oral Curcumin: Biomarkers of Systemic Activity and Compliance, Clinical Cancer Research, vol. 10, 6847-6854 (Oct. 15, 2004).
Hong CH, Kim Y, and Lee SK, Sesquiterpenoids from the Rhizone of Curcuma Zedoarin, Arch Pharm Res., 24(5): 424-426 (2001).
G. Scapagnini, R Foresti, V, Calabrese, AM Giufirida Stella, CJ Green, and R. Motterlini, Caffeic Acid Phenethyl Ester and Curcumin: A Novel Class of Heme Oxygenase-1 Inducers, Molecular Pharmacology, 61(3):554-561 (2002).
Supplementary European Search Report (3 pages) dated Dec. 14, 2009.
Anna Carolina CM Manzan, Toniolo FS, Bredow E, and Povh, NP, Extraction of Essential Oil and Pigments from Curcuma longa [L] by Steam Distillation and Extraction with Volatile Solvents, Journal of Agricultural and Food Chemistry, 51:6802-6807 (2003).
Negi PS, Jayaprakasha GK, Rao LJM, and Sarkaria KK, Antibacterial Activity of Turmeric Oil: A Byproduct from Curcumin Manufacture, J. Agric, Food Chem., 47:4297-4300 (1999).

(56) References Cited

OTHER PUBLICATIONS

Hong CH, Noh MS, Lee WY and Lee SK, Inhibitory Effects of Natural Sesquiterpenoids Isolated from the Rhizomes of *Curcuma zedoaria* on Prostaglandin $E_2$ and Nitric Oxide Production, Planta Med, 68:545-547.
Craig WJ, The Golden Touch of Turmeric, Vibrant Life, 19 (3): 38-39 (2003), ProQuest Central.
Sandur SK, Pandey MK, Sung B, Ahn KS, Murakami A, Sethi G, Limtrakul P, Badmaev V and Aggarwal BB, Curcumin Demethoxycurcumin, Bisdemethoxycurcumin, Tetrahydrocurcumin and Turmerones Differentially Regulate Anti-Inflammatory and Anti-Proliferative Responses Through a ROS-Independent Mechanism, Carcinogenesis Advance Access, originally published online on May 23, 2007, Carcinogenesis 28(8):1765-1773 (2007): doi:10.1093/carcin/bgm123.
Asche SL and Thakkar SK, Oil Extraction increases Curcumin Availability from Turmeric Sources, FASEB Journal, 18(4-5): Abstract 115.7 (2004).
Fujii Masami et al, Ingredient that improves bio-availability of curcumin, latest edition of Natural Food coloring material, Korin Publishing Co., Ltd., pp. 168-172 (2001).
Janaki, N and Bose, JL, An Improved Method for the Isolation of Curcumin From Tumeric, Curcuma Longa, I., Journal of Indian Chemical Society, 44(11):985-986 (1967).
Krishnamurthy, N, Mathew, AG, Nambudiri, ES, Shivashankar, S, Lewis, YS, and Natarajan, CP, Oil and Oteoresin of Tumeric, Trop, Sci., 18(1):37-45 (1976).
Huang, M-T, Lou, Y-R, MA, W, Newmark, HL, Reuhl, KR and Conney, AH, Inhibitory Effects of Dietary Curcumin on Forestomach. Duodenal, and Colon Carcinogenesis in Mice, Cancer Research, 54:5841-5847 (1994).
Pabon, HJJ, A Synthesis of Curcumin and Related Compounds, Recueil, 83:379-386 (1964).
Xu, Y, Ku, B-S, Yao, H-Y, Lin, Y-H, MA, X, Zhang, Y-H, Li, X-J, Antidepressant effects of curcumin in the forced swim test and olfactory bulbectomy models of depression in rats. Pharmacology Biochemistry and Behavior, 82(1):200-206 (2005), Elsevier, Inc.
Yu, ZF, Kong, LD, and Chen, Y, Antidepressant activity of aqueous extracts of *Curcuma long* in mice, Journal of Ethnopharmacology, 83(1-2): 161-165 (2002), Elsevier Science Ireland Ltd.

Funk, JL, Oyarzo, JN, Frye, JB, Chen, G, Lantz, RC, Jolad, SD, Solyom, AM, and Timmermann, BN, Turmeric extracts containing curcuminoids prevent experimental rheumatoid arthritis, Journal of Natural Products, 69(3):351-355 (2006), American Chemical Society and American Society of Pharmacology.
Begum, An, Jones, MR, Lim, GP, Morihara, I, Kim, P, Heath, DD, Rock, CL, Pruitt, MA, Yang, F, Hudspeth, B, Hu, S, Faull, KF, Teter, B, Cole, GM, and Frautschy, SA, Curcumin structure-function, bioavailability, and efficacy in models of neuroinflammation and Alzheimer's disease, Journal of Pharmacology and Experimental Therapeutics, 326(1): 196-208 (2008).
Zhang, L, Fiala, M, Cashman, J, Sayre, J, Espinosa, A, Mahanian, M. Zaghi, J, Badmaev, V, Graves, MC, Bernard, G and Rosenthal., M, Curcuminoids enhance amyloid-β uptake by macrophages of Alzheimer's disease patients, Journal of Alzhemier's Disease, 10(1):1-7 (2006), IOS Press and the authors.
Eight (8) pages of Supplementary European Search Report dated Sep. 10, 2013 in Application No. EP 11765176.
Grosso C, Valentao P, Ferres F and Andrade PB, The use of flavonoids in central nervous system disorders, Current Medicinal Chemistry, 20:1-26 (2013).
Bergman J, Midownik C, Bersudsky Y, Sokolik S, Lerner PP, Krenin A, Polakiewicz J and Lerner V, Curcumin as an Add-On to Antidepressive Treatment: A Randomized, Double-Blind, Placebo-Controlled, Pilot Clinical Study, Clinical Neuropharm, 36:73-77 (2013).
Guidance for Industry Estimating the Maximum Safe Starting Dose in Initial Clinical Trials for Therapeutics In Adult Healthy Volunteers: U.S. Department of Health and Human Services Food and Drug Administration Center for Drug Evaluation and Research (CDER) (referred to as "Guidance"), J:\IGUIDANC\5541fnlclnl. doc, pp. 1-27 (Jul. 6, 2005).
Lankapatiravna, Arkaprakasah, 5 (p. 04-08) (Ref.pg. no.of publication:44), Edn. 1st 1995, Krishnadas Academy, Varanasi, India.†
Sodhala, Gadanigrahah ed Ganga Sahaya Pandeya & Com.—Indradeva Tripathi Part-3(Salakya-Pancakarma Khanda), 7 (p. 09-15) (Ref.pg. No. of publication:727), Ed. 3rd 1999, Chaukhamba Sanskrit Sansthan, Varanasi, India.†
Govinda Dasa, Bhaisajya Ratnavali, 6 (p. 16-21), (Ref.pg. No.of publication:263), Edn. 14th. 2001, Chaukhamba Sanskrit Sansthan, Varanasi, India.†

\* cited by examiner
† cited by third party

TABLE 9 - ACR RESPONSE

| PARAMETER | RAW TURMERIC | | EOT WITH 45% AR-T | | EOT WITH 10-15% AR-T | | C+E WITH 45% AR-T IN 1:10 RATIO | | C+E WITH 45% AR-T IN 1:1 RATIO | | C 24% + E WITH 45% AR-T IN 10:1 RATIO | | C+E WITH 10-15% AR-T IN 10:1 RATIO | | C+E WITH 45% AR-T IN 10:1 RATIO | | CURCUMINOIDS 95% | | C+E WITH 45% AR-T IN 12:1 RATIO | |
|---|---|---|---|---|---|---|---|---|---|---|---|---|---|---|---|---|---|---|---|---|
| | BASE LINE | EOT | BASE LINE | EOT | BASE LINE | EOT | BASE LINE | EOT | BASE LINE | EOT | BASE LINE | EOT | BASE LINE | EOT | BASE LINE | EOT | BASE LINE | EOT | BASE LINE | EOT |
| TOTAL PAINFUL JOINTS | 18 | 18 | 17 | 16 | 18 | 18 | 20 | 21 | 17 | 17 | 19 | 19 | 19 | 18 | 19 | 3 | 17 | 16 | 19 | 2 |
| TOTAL SWOLLEN JOINTS | 10 | 11 | 12 | 12 | 11 | 11 | 10 | 11 | 13 | 12 | 12 | 13 | 10 | 9 | 12 | 0.5 | 11 | 10 | 13 | 0.5 |
| PATIENT'S GA | 86 | 82 | 79 | 75 | 82 | 80 | 84 | 79 | 76 | 70 | 80 | 78 | 80 | 71 | 84 | 31 | 79 | 67 | 85 | 27 |
| PHYSICIAN'S GA | 84 | 79 | 74 | 72 | 79 | 76 | 81 | 75 | 79 | 70 | 75 | 71 | 78 | 70 | 80 | 28 | 75 | 70 | 79 | 25 |
| DISABILITY INDEX, HAQ | 4 | 4 | 3.5 | 3.5 | 3.5 | 3.5 | 4 | 4 | 4.5 | 4.5 | 3.5 | 3.5 | 4 | 4 | 4.5 | 1.0 | 4 | 3.5 | 4.5 | 0.5 |

FIG. 6

TABLE 12 - JOINT PAIN MEASUREMENTS AND % RESPONSE OF PATIENTS IN EACH GROUP OVER 3 MONTHS

| TIME POINTS | CONDITION OF ILLNESS | RAW TURMERIC | EOT WITH 45% AR-T | EOT WITH 10-15% AR-T | C+E WITH 45% AR-T IN 1:10 RATIO | C+E WITH 45% AR-T IN 1:1 RATIO | C 24% + E WITH 45% AR-T IN 10:1 RATIO | C+E WITH 10-15% AR-T IN 10:1 RATIO | C+E WITH 45% AR-T IN 10:1 RATIO | CURCUM-INOIDS 95% | C+E WITH 45% AR-T IN 12:1 RATIO |
|---|---|---|---|---|---|---|---|---|---|---|---|
| T0 BASE LINE | NO | 0% | 0% | 0% | 0% | 0% | 0% | 0% | 0% | 0% | 0% |
| | MILD | 20% | 22% | 15% | 18% | 13% | 20% | 20% | 14% | 13% | 13% |
| | MODERATE | 74% | 69% | 80% | 76% | 80% | 75% | 75% | 78% | 80% | 80% |
| | SEVERE | 6% | 9% | 5% | 6% | 7% | 5% | 5% | 7% | 6% | 7% |
| T12 END OF STUDY | NO | 1% | 0% | 0% | 0% | 0% | 0% | 0% | 17% | 2% | 19% |
| | MILD | 18% | 23% | 14% | 16% | 14% | 21% | 22% | 53% | 16% | 52% |
| | MODERATE | 75% | 68% | 78% | 77% | 79% | 74% | 73% | 30% | 76% | 29% |
| | SEVERE | 6% | 9% | 8% | 7% | 7% | 5% | 5% | 0% | 6% | 0% |

FIG. 7

TABLE 13 JOINT LINE TENDERNESS AND %RESPONSE OF PATIENTS IN EACH GROUP OVER 3 MONTHS

| TIME POINTS | CONDITION OF ILLNESS | RAW TURM-ERIC | EOT WITH 45% AR-T | EOT WITH 10-15% AR-T | C+E WITH 45% AR-T IN 1:10 RATIO | C+E WITH 45% AR-T IN 1:1 RATIO | C 24% + E WITH 45% AR-T IN 10:1 RATIO | C+E WITH 10-15% AR-T IN 10:1 RATIO | C+E WITH 45% AR-T IN 10:1 RATIO | CURCUM-INOIDS 95% | C+E WITH 45% AR-T IN 12:1 RATIO |
|---|---|---|---|---|---|---|---|---|---|---|---|
| T0 BASE LINE | NO JOINT LINE TENDERNESS | 12% | 15% | 14% | 11% | 15% | 11% | 13% | 14% | 12% | 13% |
|  | JOINT LINE TENDERNESS PRESENT | 88% | 85% | 86% | 89% | 85% | 89% | 87% | 86% | 88% | 87% |
| T12 END OF STUDY | NO IMPROVED | 13% 2% | 15% 1% | 14% 2% | 11% 1% | 15% 3% | 12% 1% | 15% 6% | 50% 50% | 14% 7% | 52% 48% |
|  | SAME WORSENED | 85% 0% | 84% 0% | 84% 0% | 88% 0% | 82% 0% | 87% 0% | 79% 0% | 0% 0% | 79% 0% | 0% 0% |

*FIG. 8*

TABLE 14 - WALKING DISTANCE SCORES AND % RESPONSE OF PATIENTS IN EACH GROUP OVER 3 MONTHS

| TIME POINTS | CONDITION OF ILLNESS | RAW TURMERIC | EOT WITH 45% AR-T | EOT WITH 10-15% AR-T | C+E WITH 45% AR-T IN 1:10 RATIO | C+E WITH 45% AR-T IN 1:1 RATIO | C 24% + E WITH 45% AR-T IN 10:1 RATIO | C+E WITH 10-15% AR-T IN 10:1 RATIO | C+E WITH 45% AR-T IN 10:1 RATIO | CURCUM-INOIDS 95% | C+E WITH 45% AR-T IN 12:1 RATIO |
|---|---|---|---|---|---|---|---|---|---|---|---|
| T0 BASE LINE | <100 M<br>100-500 M<br>500-1000 M<br>>1000 M | 7%<br>29%<br>33%<br>31% | 9%<br>31%<br>40%<br>20% | 10%<br>29%<br>38%<br>23% | 8%<br>35%<br>42%<br>15% | 7%<br>34%<br>41%<br>18% | 9%<br>33%<br>44%<br>14% | 10%<br>27%<br>45%<br>18% | 7%<br>37%<br>35%<br>21% | 8%<br>23%<br>46%<br>23% | 8%<br>35%<br>39%<br>18% |
| T12 END OF STUDY | <100 M<br>100-500 M<br>500-1000 M<br>>1000 M | 7%<br>28%<br>33%<br>32% | 9%<br>30%<br>41%<br>20% | 10%<br>29%<br>38%<br>23% | 8%<br>33%<br>40%<br>15% | 6%<br>33%<br>42%<br>19% | 9%<br>32%<br>44%<br>15% | 9%<br>25%<br>47%<br>19% | 0%<br>0%<br>28%<br>72% | 7%<br>21%<br>47%<br>25% | 0%<br>3%<br>22%<br>75% |

*FIG. 9*

FORMULATION OF CURCUMIN WITH ENHANCED BIOAVAILABILITY OF CURCUMIN AND METHOD OF PREPARATION AND TREATMENT THEREOF

This application is a divisional of co-pending U.S. application Ser. No. 13/645,031 filed Oct. 4, 2012, which is a continuation-in-part of PCT Application Serial No. PCT/IN2011/000232, filed Apr. 4, 2011, which claims priority of Indian Provisional Application Serial No. 950/CHE/2010, filed Apr. 5, 2010, and a continuation-in-part of co-pending U.S. application Ser. No. 14/094,725, filed Dec. 2, 2013, which is a divisional of U.S. application Ser. No. 13/385,717, filed Mar. 5, 2012, which is a divisional of Ser. No. 12/926,985 filed Dec. 21, 2010, which is a divisional of Ser. No. 12/662,740 filed Apr. 30, 2010, which is a divisional of U.S. application Ser. No. 11/635,599 filed Dec. 8, 2006, which is a continuation of PCT Application Serial No. PCT/IN05/00176, filed May 30, 2005, and a continuation-in-part of co-pending U.S. application Ser. No. 13/674,249, filed Nov. 12, 2012, which is a divisional of Ser. No. 13/506,572, filed Apr. 30, 2012, which is a divisional of Ser. No. 12/926,980, filed Dec. 21, 2010, which is a divisional of Ser. No. 12/073,864, filed Mar. 11, 2008, which is a continuation-in-part of Ser. No. 11/635,599, filed Dec. 8, 2006, which is a continuation of PCT Application Serial No. PCT/IN05/00176, filed May 30, 2005, all of which applications are incorporated in entirety by reference. U.S. application Ser. No. 13/645,031 filed Oct. 4, 2012, is a continuation-in-part of U.S. application Ser. No. 13/385,717, filed Mar. 5, 2012, which is a divisional of Ser. No. 12/926,985 filed Dec. 21, 2010, which is a divisional of Ser. No. 12/662,740 filed Apr. 30, 2010, which is a divisional of U.S. application Ser. No. 11/635,599 filed Dec. 8, 2006, which is a continuation of PCT Application Serial No. PCT/IN05/00176, filed May 30, 2005; and, a continuation-in-part of Ser. No. 13/506,572, filed Apr. 30, 2012, which is a divisional of Ser. No. 12/926,980, filed Dec. 21, 2010, which is a divisional of Ser. No. 12/073,864, filed Mar. 11, 2008, which is a continuation-in-part of Ser. No. 11/635,599, filed Dec. 8, 2006, which is a continuation of PCT Application Serial No. PCT/IN05/00176, filed May 30, 2005, all of which applications are incorporated in entirety by reference.

OBJECTIVE OF THE INVENTION

The following specification describes an invention which relates to a formulation of curcuminoid with essential oil of turmeric to enhance the bioavailability of curcumin and to augment the biological activity of curcumin, wherein curcumin is the main constituent of curcuminoid and wherein Ar-turmerone is the main constituent of the essential oil of turmeric. Such enhanced bioavailability of curcumin has been demonstrated in human volunteers. The present invention also relates to an application of curcuminoid with essential oil of turmeric to enhance the bioavailability of curcumin for oral supplementation against a variety of diseases and method of doing the same. In particular the present invention relates to oral supplementation of curcuminoid with essential oil of turmeric to enhance the bioavailability of curcumin for the prophylaxis, treatment, maintenance therapy and as add on therapy for disease conditions such as cancer, heart diseases, diabetes, rheumatoid arthritis, osteoarthritis, alzheimer's disease, inflammatory bowel diseases, liver fibrosis and cirrhosis, abdominal aortic aneurysms, HIV, pancreatitis, drug-resistant malaria, psoriasis, cystic fibrosis, epilepsy, wound healing, diseases of the central nervous system, chronic degenerative diseases and potentially many other diseases where better delivery of curcumin from the supplement to the blood and tissues is critical fir the enhanced therapeutic benefit and an improved method of delivering curcumin and ensuring bioavailability in humans.

BACKGROUND OF THE INVENTION

Curcumin [1,7-bis(4-hydroxy-3-methoxyphenyl)-1,6-heptadiene-3,5-dione]

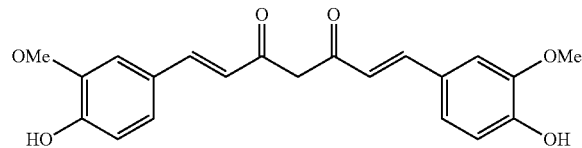 [SMILES: COc1cc(/C=C/C(=O)CC(=O)/C=C/c2ccc(O)c(OC)c2)ccc1O]

is the major yellow pigment of turmeric, a commonly used spice, derived from the rhizome of the herb *Curcuma longa* Linn. In the Indian subcontinent and Southeast Asia, turmeric has traditionally been used as a treatment for inflammation, skin wounds, and tumors. Clinical activity of curcumin is yet to be confirmed; however, in preclinical animal models, curcumin has shown cancer chemo preventive, antineoplastic and anti-inflammatory properties[1]. Especially interesting is its ability to prevent the formation of carcinogen-induced intestinal premalignant lesions and malignancies in rat[2,3] and in the multiple neoplasia (Min/+) mouse[4], a genetic model of the human disease familial adenomatous polyposis. Curcumin acts as a scavenger of oxygen species such as hydroxyl radical, superoxide anion and singlet oxygen[5,6,7] and interferes with lipid peroxidations[8,9]. Curcumin suppresses a number of key elements in cellular signal induction pathways pertinent to growth, differentiation and malignant transformations. Among signaling events inhibited by curcumin are protein kinases[10], c-Jun/AP-1 activation[11], prostaglandin biosynthesis[12] and activity and expression of the enzyme cyclooxygenase-2[13,14]. This latter property is probably mediated by the ability of curcumin to block activation of the transcription factor NF-κB at the level of the NF-κB inducing kinase/IKKα/β signalling complex[15].

Curcumin directly inhibits cyclooxygenase-2 and also inhibits the transcription of the gene responsible for its production. Cyclooxygenases (COX) catalyze the synthesis of prostaglandins (PGs) from arachidonic acid. There are two isoforms of COX, designated COX-1 and COX-2. COX-1 is expressed constitutively in most tissues and appears to be responsible for housekeeping functions[16] while COX-2 is not detectable in most normal tissues but is induced by oncogenes, growth factors, carcinogens and tumor promoters[17,18,19]. Several different mechanisms account for the link between COX-2 activity and carcinogenesis.

Curcumin is not simply an alternative to non-steroidal anti-inflammatory drugs (NSAIDS), which also have anti-inflammatory and cancer chemopreventive properties. This is so because COX is a bifunctional enzyme with cyclooxygenase and peroxidase activities. Aside from being important for PG synthesis, the peroxidase function contributes to the activation of procarcinogens. Therefore, the failure of NSAIDS to inhibit the peroxidase function of COX potentially limits their effectiveness as anticancer agents. Curcumin, in contrast, down-regulates levels of COX-2 and thereby decreases both the cyclooxygenase and peroxidase activities of the enzyme.

Curcumin is among the few agents to block both the COX and LOX (lipoxygenase) pathways of inflammation and carcinogenesis by directly modulating arachidonic acid metabolism. In a study to evaluate the effect of curcumin on the metabolism and action of arachidonic acid in mouse epidermis, it was found that topical application of curcumin inhibited arachidonic acid-induced ear inflammation in mice[20]. Curcumin (10 μM) inhibited the conversion of arachidonic acid to 5- and 8-hydroxyeicosatetraenoic acid by 60% and 51%, respectively (LOX pathway) and the metabolism to PGE2, PGF2α and PGD2 by 70%, 64% and 73%, respectively (COX pathway). In another study, dietary administration of 0.2% curcumin to rats inhibited azoxymethane-induced colon carcinogenesis and decreased colonic and tumor phospholipase A2, phospholipase Cγ1, and PGE2 levels[21]. In this study, dietary curcumin also decreased enzyme activity in the colonic mucosa and tumors for the formation of PGE2, PGF2α, PGD2, 6-keto-PGF2α and thromboxane B2 via the COX system and production of 5(S)-, 8(S)-, 12(S)-, and 15(S)-hydroxy-eicosatetraenoic acid via the LOX pathway was also inhibited.

Despite this impressive array of beneficial bioactivities, the bioavailability of curcumin in animals and man remains low. In rodents, curcumin demonstrates poor systemic bioavailability after p.o. dosing[22] which may be related to its inadequate absorption and fast metabolism. Curcumin bioavailability may also be poor in humans as seen from the results of a recent pilot study of a standardized turmeric extract in colorectal cancer patients[23]. Indirect evidence suggests that curcumin is metabolized in the intestinal tract. Curcumin undergoes metabolic O-conjugation to curcumin glucuronide and curcumin sulfate and bioreduction to tetrahydrocurcumin, hexahydrocurcumin and hexahydrocurcuminol in rats and mice in vivo[24,25] in suspensions of human and rat hepatocytes[26] and in human and rat intestine[27]. Metabolic conjugation and reduction of curcumin was more in human than in rat intestinal tissue. It has been suggested that the intestinal tract plays an important role in the metabolic disposition of curcumin. This is based predominantly on experiments in which [$^3$H] labeled curcumin was incubated with inverted rat gut sacs[28]. This was later confirmed in intestinal fractions from humans and rats. Intestinal mucosa, as well as liver and kidney tissue from the rat, can glucorodinate and sulfate curcumin, as judged by the analysis of differential amounts of curcumin present before and after treatment of tissue extracts with conjugate-hydrolyzing enzymes[29]. Thus, gut metabolism contributes substantially to the overall metabolic yield generated from curcumin in vivo. In human intestinal fractions, conjugation with activated sulfuric or glucuronic acids was much more abundant, whereas conjugation in human hepatic tissues was less extensive, than in the rat tissues[30].

Although p.o. administered curcumin has poor bioavailability and only low or non-measurable blood levels were observed[31], this route of administration inhibits chemically induced skin and liver carcinogenesis[32,33]. Oral administration of curcumin also inhibits the initiation of radiation-induced mammary and pituitary tumors[34]. Similarly, in a study to assess the curcumin levels in the colorectum, a daily dose of 3.6 g curcumin achieves pharmacologically effective levels in the colorectum with negligible distribution of curcumin outside the gut[35].

Earlier Shobha et al[36] had observed that administering piperine along with curcumin enhances the bioavailability of curcumin. However, the level of enhancement was only modest and no curcumin could be detected after 3 hours even when supplemented with piperine.

Although some questions remain unanswered regarding the pharmacokinetics of curcumin in humans, there is no denying the fact that considerable proportion of ingested curcumin is excreted through feces and at least about one-half of absorbed curcumin is metabolized. The quantity of curcumin that reaches tissues outside the gut is probably pharmacologically insignificant. Several studies have failed to demonstrate the positive in vitro results with curcumin in in vivo animal and human studies due to lack of absorption of curcumin after oral administration. To provide the clinical benefits, curcumin must be absorbed from its oral route of administration at a suitable rate, be distributed in adequate concentration in the blood and remain in the system for a sufficient period at an effective concentration level.

SUMMARY

Some embodiments provide a composition of a curcuminoid mixture and added essential oil of turmeric. In some embodiments, the weight ratio of the curcuminoid mixture to the added essential oil of turmeric ranges from about 1:3 to about 99:1. In some embodiments, the curcuminoid mixture includes curcumin, demethoxycurcumin and bisdemethoxycurcumin. In some embodiments, the essential oil of turmeric includes ar-turmerone. In some embodiments, the essential oil of turmeric includes about 40-50% ar-turmerone.

Some embodiments provide a method of treating rheumatoid arthritis by administering a composition having a curcuminoid mixture and added essential oil of turmeric.

Some embodiments provide a method of reducing visual analogue scale for pain by administering a composition having curcuminoid mixture and added essential oil of turmeric.

Some embodiments provide a method of decreasing disease activity score by administering a composition having the curcuminoid mixture and added essential oil of turmeric. Some embodiments provide a method of improving patient response to ACR criteria by administering composition of a curcuminoid mixture and added essential oil of turmeric. Some embodiments provide a method of reducing C-reactive protein levels by administering a composition of a curcuminoid mixture and added essential oil of turmeric. Some embodiments provide a method of reducing rheumatoid Arthritis Factor by administering a composition of a curcuminoid mixture and added essential oil of turmeric. Some embodiments provide a method of decreasing joint pain by administering a composition of a curcuminoid mixture and added essential oil of turmeric. Some embodiments provide a method of improving walking distance scores by administering a composition of a curcuminoid mixture and added essential oil of turmeric. Some embodiments provide a method of treating osteoarthritis by administering a composition of a curcuminoid mixture and added essential oil of turmeric. Some embodiments provide a method of treating Alzheimer's disease by administering a composition of a curcuminoid mixture and added essential oil of turmeric. Some embodiments provide a method of improving mini mental state exam scores by administering a composition of a curcuminoid mixture and added essential oil of turmeric. Some embodiments provide a method of increasing Vitamin E levels by administering a composition of a curcuminoid mixture and added essential oil of turmeric. Some embodiments provide a method of increasing serum amyloid beta levels by administering a composition of a curcuminoid mixture and added essential oil of turmeric. Some embodiments provide a method of disaggregating amyloid beta by administering a composition of a curcuminoid mixture and added essential oil of turmeric. Some embodiments provide a method of lowering plasma isoprostane levels by administering a composition of a curcuminoid mixture and added essential oil of turmeric. Some embodiments provide a method of treating depression by administering a composition of a curcuminoid mixture and added essential oil of turmeric. Some embodiments provide a method of improving response rate on Hamilton Depression rate scale by administering a composition of a curcuminoid mixture and added essential oil of turmeric. Some embodiments provide a method if improving clinical global impression by Global Severity comprising administering a composition of a curcuminoid mixture and added essential oil of turmeric. Some embodiments provide a method of improving clinical global impression by Global Change scale by administering a composition of a curcuminoid mixture and added essential oil of turmeric.

BRIEF DESCRIPTION OF THE DRAWINGS

The above objectives and advantages of the disclosed teachings will become more apparent by describing in detail preferred embodiments thereof with reference to the attached drawings in which:

FIG. 6 provides Table 9 (ACR response of different groups)

FIG. 7 provides Table 12 (Joint pain measurements and % response of patients in each group over 3 months)

FIG. 8 provides Table 13 (Joint line tenderness and % response of patients in each group over 3 months)

FIG. 9 provides Table 14 (Walking distance scores and % response of patients in each group over 3 months)

DETAILED DESCRIPTION

Figure 1:
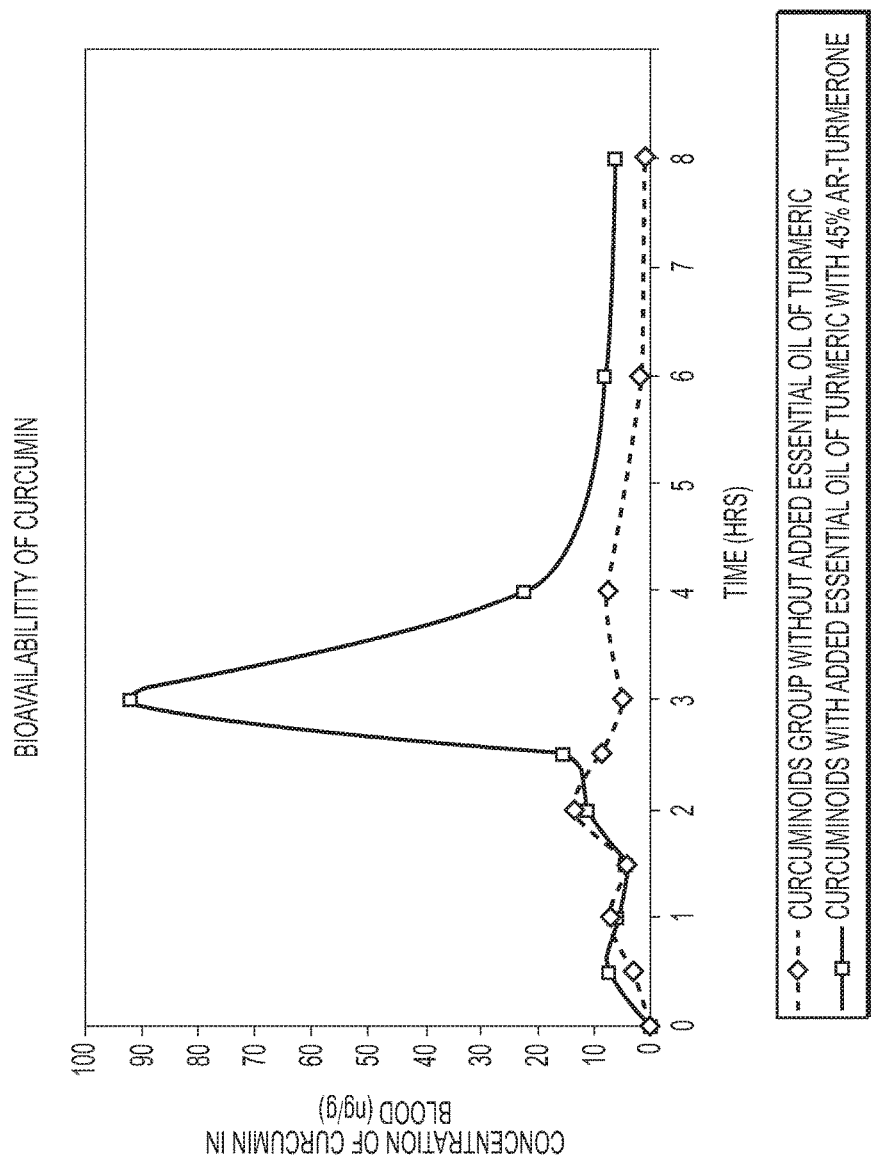
FIG. 1 provides a graph showing the bioavailability of curcumin in humans upon administration of (1) gelatin capsules, which were prepared by admixing curcuminoid isolated from turmeric with essential oil of turmeric, and, (2) gelatin capsules of curcuminoid alone, which were prepared without adding essential oil of turmeric to the curcuminoid isolated from turmeric. The x-axis shows time in hours following administration of the gelatin capsules. The y-axis shows the concentration of curcumin (ng/g) in blood FIG. 2 provides a graph showing the bioavailability of curcumin in human upon administration of 1) gelatin capsule, which were prepared by admixing curcuminoid with added essential oil of turmeric with 45% Ar-turmerone in 10:1 ratio, 2) gelatin capsules of curcuminoid alone, which were prepared without adding essential oil of turmeric to the curcuminoid isolated from turmeric, 3) gelatin capsules of raw turmeric powder alone, 4) gelatin capsules of Essential oil of turmeric with 45% Ar-turmerone alone, 5) gelatin capsules of essential oil of turmeric with 10-15% Ar-turmerone alone, 6) gelatin capsule, which were prepared by admixing curcuminoid with added essential oil of turmeric with 45% Ar-turmerone in 12:1 ratio, The x-axis shows time in hours and y-axis shows the concentration of curcumin (ng/g) in blood FIG. 3 provides a comparison of the bioavailability of curcumin from the curcuminoid mixture without added essential oil of turmeric group and the curcuminoid mixture with added essential oil of turmeric with 45% Ar-turmerone in a weight ratio ranging from about 1:3 to 99:1. The x-axis shows the ratio of curcumin to essential oil of turmeric and y-axis shows the AUC value of curcumin FIG. 4 provides a comparison of curcumin bioavailability from 10:1 and 1:10 weight ratios of 1) curcuminoid (454.55 mg) with added essential oil of turmeric (45.45 mg) with 45% Ar-turmerone in 10:1 ratio, 2) curcuminoid (20 mg) with added essential oil of turmeric (2 mg) with 45% Ar-turmerone in 10:1 ratio, 3) curcuminoid (20 mg) with added essential oil of turmeric (200 mg) with 45% Ar-turmerone in 1:10 ratio, 4) curcuminoid (20 mg) with added essential oil of turmeric (200 mg) with 10-15% Ar-turmerone in 1:10 ratio, 5) curcuminoid alone (454.55 mg), 6) curcuminoid alone (20 mg), 7) Essential oil of turmeric with 45% Ar-turmerone alone (45.45 mg), 8) Essential oil of turmeric with 10-15% Ar-turmerone alone (200 mg). The x-axis shows time in hours and y-axis shows the concentration of curcumin (ng/g) in blood FIG. 5 provides Method of preparation of Essential oil of turmeric with varying concentration of Ar-turmerone.

The disclosure relates to a product to enhance the bioavailability of curcumin by mixing a suitable portion of the volatile oil obtained from turmeric with the curcuminoids isolated from turmeric.

As disclosed herein the term "curcuminoid" is a mixture of curcumin, demethoxycurcumin and bisdemethoxycurcumin. In some embodiments, curcumin is the major component of the curcuminoid mixture. In some embodiments, demethoxycurcumin and bisdemethoxycurcumin are minor components of the curcuminoid mixture. In some embodiments, 95% of the crystals having curcuminoid mixture are composed of curcumin, demethoxycurcumin and bisdemethoxycurcumin.

The term "essential oil" or "essential oil of turmeric" is also referred to as "volatile oil" or "volatile oil of turmeric." The essential oil of turmeric is a mixture of oils. Essential oil is obtained as a by-product during the extraction of curcumin or curcuminoids from turmeric. In some embodiments, Ar-turmerone, which is also referred to as turmerone, is the main constituent of essential oil. In some embodiments, Ar-turmerone constitutes about 40-50% of the essential oil of turmeric. In some embodiments, Ar-turmerone comprises about 45% of the essential oil of turmeric.

As stated herein, the term "a" or "an" refers to one or more.

As stated herein, the terms "isolated" and "purified" are referred to interchangeably.

The volatile oil of turmeric was isolated by conventional methods of steam distillation to isolate essential oils and is well known in the art.

Curcumin is isolated from the de-oiled turmeric by solvent extraction. Suitable solvents for this purpose include acetone, hexane, ethyl acetate, dicholoroethane, chloroform, etc. The extraction is conveniently carried out at moderate temperatures (40-55° C.) and the solvent is partially removed to yield a concentrate containing 30-60% solids. This solution is cooled to obtain crystals of curcuminoid which are isolated by any suitable method such as filtration or centrifugation. Analysis of this product, which is composed of the isolated crystals of curcumioid mixture, showed that, in some embodiments, 95% of the product was composed of curcumin, demethoxycurcumin and bisdemethoxycurcumin.

The disclosure provides a composition having curcuminoid and an essential oil of turmeric. Curcumin and the volatile oils of curcumin are mixed and blended to get a uniform product. If small percentages (~5%) of the essential oil of turmeric are added to the curcuminoid, then the bioavailability of curcumin is significantly enhanced. Accordingly, a composition of curcuminoid admixed with a suitable proportion of Ar-turmerone (the main component of the turmeric essential oil) is provided.

In some embodiments, the weight ratio of the curcuminoid to the essential oil of turmeric ranges from about 1:1 to about 90:1. In some embodiments, the weight ratio of the curcuminoid to the essential oil of turmeric ranges from about 1:1 to about 3:1. The weight ratio of the curcuminoid to the essential oil of turmeric can be varied from about 3:1 to about 99:1. In some embodiments, the weight ratio of the curcuminoid to the essential oil of turmeric ranges from about 1:1 to about 70:1. In some embodiments, the weight ratio of the curcuminoid to the essential oil of turmeric ranges from about 1:1 to about 45:1. In some embodiments, the weight ratio of the curcuminoid to the essential oil of turmeric ranges from about 3:1 to about 50:1. In some embodiments, the weight ratio of the curcuminoid to the essential oil of turmeric ranges from about 8:1 to about 25:1. In some embodiments, the weight ratio of the curcuminoid to the essential oil of turmeric is about 90:7. In some embodiments, the weight ratio of the curcuminoid to the essential oil of turmeric is about 90:8. In some embodiments, the weight ratio of the curcuminoid to the essential oil of turmeric is about 90:9. In some embodiments, the weight ratio of the curcuminoid to the essential oil of turmeric is about 89:9. In some embodiments, the weight ratio of the curcuminoid to the essential oil of turmeric is about 89:8. In one embodiment, the ratio is about 85:15. In another embodiment, the ratio is about 92:8. In another embodiment, the ratio is about 95:5. In another embodiment the weight ratio is about 10:1. In some embodiments, the weight ratio is about 12:1. In some embodiments, the weight ratio of the curcuminoid to the essential oil of turmeric is about 1:2. In some embodiments, the weight ratio of the curcuminoid to the essential oil of turmeric is about 2:1. In some embodiments, the weight ratio of the curcuminoid to the essential oil of turmeric ranges from about 1:3 to about 99:1. In some embodiments of the composition having curcuminoid and added essential oil of turmeric, the curcuminoid ranges, by weight, from about 24% to about 96%. In some embodiments of the composition having curcuminoid and added essential oil of turmeric, the curcuminoid ranges, by weight, from about 30% to about 96%. In some embodiments of the composition of curcuminoid and added essential oil of turmeric, the curcuminoid ranges, by weight, from about 40% to about 75%. In some embodiments of the composition having curcuminoid and added essential oil of turmeric, the curcuminoid ranges, by weight, from about 50% to about 60%.

In some embodiments of the composition having curcuminoid and added essential oil of turmeric, the demethoxycurcumin ranges, by weight, from about 5% to about 25%. In some embodiments of the composition having curcuminoid and added essential oil of turmeric, the demethoxycurcumin ranges, by weight, from about 10% to about 20%.

In some embodiments of the enhanced curcumin bioavailability composition having curcuminoid and added essential oil of turmeric, the bisdenmethoxycurcumin ranges, by weight, from about 2% to about 7%.

In some embodiments of the enhanced curcumin bioavailability composition having curcuminoid and added essential oil of turmeric, the essential oil of turmeric ranges, by weight, from about 4% to about 50%. In some embodiments, of the composition of curcuminoid and added essential oil having turmeric, the essential oil of turmeric ranges, by weight, from about 15% to about 50%. In some embodiments of the composition having curcuminoid and added essential oil of turmeric, the essential oil of turmeric ranges, by weight, from about 20% to about 50%. In some embodiments of the composition having curcuminoid and added essential oil of turmeric, the essential oil of turmeric ranges, by weight, from about 25% to about 40%.

Some embodiments include a composition having a curcuminoid and an added amount of essential oil of turmeric, wherein the essential oil is present in an amount sufficient to cause an enhancement of bioavailability of the curcumin when administered to a human as compared to the bioavailability of curcumin upon administration of a composition prepared using curcuminoid alone without adding essential oil. Curcumin levels in blood samples is greater following administration of a composition having curcuminoid and added essential oil of turmeric as compared to a composition of curcuminoid alone. In some embodiments, the enhancement of bioavailability of curcumin following administration of a composition of curcuminoid and added essential oil of turmeric ranges from about 5-fold to about 16-fold. Enhancement of bioavailability of curcumin from a composition prepared by mixing curcuminoid and essential oil of turmeric is provided in FIG. 1 and Example 1.

In some embodiments, a composition of a curcuminoid and added essential oil of turmeric is orally administered to a human.

A method of extraction of curcuminoids includes treating dried and powdered rhizomes of turmeric with a solvent, followed by solvent stripping, and steam distilling to obtain an essential-oil free extract. The essential oil-free extract is cooled to about 4° C. to allow the curcuminoids to crystallize. The curcuminoids are then separated by filtration, centrifugation or any other method of solid-liquid separation well-known in the art. In some embodiments, 95% of the separated crystals are composed of curcumin, demethoxycurcumin and bisdemethoxycurcumin.

Curcumin is isolated from the de-oiled turmeric by solvent extraction. Suitable solvents for this purpose include acetone, hexane, ethyl acetate, dicholoroethane, chloroform, etc. The extraction is conveniently carried out at moderate temperatures (about 40° C. to about 55° C.) and the solvent is partially removed to yield a concentrate containing 30-60% solids. This solution is cooled to obtain crystals having curcuminoid mixture which are isolated by any suitable method such as filtration or centrifugation. 95% of this product (crystals) was composed of the curcuminoid mixture. The remaining may contain traces of essential oil plus other constituents such as carbohydrates, etc, which were not characterized.

The disclosure provides a method of extracting a curcuminoid from turmeric including:
drying rhizomes of turmeric to form a dried turmeric;
powdering the dried turmeric to form a powdered turmeric;
treating the powdered turmeric with a solvent selected from the group consisting of ethyl acetate, acetone, hexane, ethylene dichloride, ethyl alcohol, and combinations thereof to form a solution;
stripping the solvent from the solution to form an extract;
cooling the extract to about 4° C. to form crystals and a liquid, wherein the liquid comprises the essential oil of turmeric and a resin; and
separating the crystals from the liquid to obtain the curcuminoid crystals.

In some embodiments, curcumin, demethoxycurcumin and bisdemethoxycurcumin comprise 95% of the curcuminoid crystals.

Some embodiments include a method of extracting a curcuminoid from turmeric by drying rhizomes of turmeric to form dried turmeric. The dried turmeric is powdered to form powdered turmeric. The powdered turmeric is treated with a solvent selected from the group consisting of ethyl acetate, acetone, hexane, and combinations thereof to form a solution. The solvent is stripped from the solution to form an extract. The extract is cooled to about 4° C. to form crystals having curcuminoid mixture, and, a liquid. The liquid comprises the essential oil of turmeric and a resin. The crystals having the curcuminoid mixture are separated from the liquid. In some embodiments, 95% of the crystals having the curcuminoid mixture is composed of the curcuminoid mixture, namely, curcumin, demethoxycurcumin and bisdemethoxycurcumin.

The volatile oil of turmeric was isolated by conventional methods of steam distillation to isolate essential oils and is well known in the art.

Curcuminoid and the essential oil are blended in a suitable proportion by a process including, suspending the curcuminoid in about 3 to 5 times its quantity of water, mixing in the essential oil, pulverizing in a colloidal mill into fine slurry, and stripping the slurry off water under heat and vacuum to obtain a uniform blend. Five hundred milligram capsules are made from this blend for human consumption.

The disclosure provides a method of preparing a composition including a curcuminoid and an essential oil of turmeric including:
suspending the curcuminoid in water to form a suspension;
adding the essential oil to the suspension to form a mixture;
homogenizing the mixture to obtain a fine slurry; and
drying the fine slurry under heat and vacuum to form a uniform blend of a composition including the curcuminoid and the essential oil of turmeric. Drying of the fine slurry under heat and vacuum can be performed using a vaccumized desolventiser with a stirrer.

A composition of curcuminoid and added essential oil of turmeric can be prepared by suspending the curcuminoid in water to form a suspension. Essential oil is added to the suspension to form a mixture. The mixture is homogenized to form fine slurry. The fine slurry is dried under heat and vacuum to form a uniform blend of a composition of curcuminoid and an essential oil of turmeric. The fine slurry can be dried under heat and vacuum using, for example, a vaccumized desolventiser having a stirrer.

In one embodiment, a homogeneous mixture of curcuminoid and water is prepared by suspending the curcuminoid in water to form a suspension. The suspension is homogenized to obtain fine slurry. The fine slurry is dried under heat and vacuum to form a composition having a homogeneous mixture of the curcuminoid and water.

The disclosure provides a method of preparing a homogeneous mixture having a curcuminoid and water by,
suspending a curcuminoid in water to form a suspension;
homogenizing the suspension to obtain a fine slurry; and
drying the suspension under heat and vacuum to form a composition including a homogeneous mixture of the curcuminoid and water.

Hard gelatin capsules, which contain about 500 mg of a blend of curcuminoid and essential oil of turmeric, are prepared. A 500 mg capsule for enhanced bioavailability of curcumin, having the curcuminoid mixture and essential oil of turmeric in a weight ratio of about 95:5 is expected to contain about 460 mg of curcuminoid and about 40 mg of essential oil. The curcuminoid mixture is composed of curcumin, demethoxycurcumin and bisdemethoxycurcumin. In terms of active constituents, the respective figures would be about 437 mg of curcumin and about 18 mg of Ar-turmerone. In some embodiments, the gelatin capsules have about 300 mg to about 460 mg of curcuminoid and about 40 mg to about 375 mg of essential oil of turmeric. In some embodiments of the composition having curcumin and added essential oil of turmeric, wherein the gelatin capsule comprises 500 mg of a blend including the curcuminoid and the essential oil, the curcuminoid in the blend ranges from about 300 mg to about 485 mg, and the Ar-turmerone in the blend ranges from about 5 mg to about 200 mg.

Gelatin capsules with curcuminoid alone but without added essential oil were similarly prepared to study the comparative efficacies of the capsule containing added essential oil versus the capsule prepared without adding essential oil.

The disclosure provides a method of preparing a gelatin capsule having a curcuminoid and an essential oil of turmeric by suspending a curcuminoid in water to form a suspension. Then adding an essential oil to the suspension to form a mixture. Then homogenizing the mixture to obtain a fine slurry. Then drying the slurry under heat and vacuum to form a uniform blend of a composition having the curcuminoid and the essential oil of turmeric. Then compressing the blend into the hard gelatin capsule.

Hard gelatin capsules of a composition having a curcuminoid and an added essential oil of turmeric can be prepared by compressing a uniform blend of the composition into a capsule. Gelatin capsules are prepared by standard methods using instrument such as a capsule filling machine manufactured by Pam Pharmaceuticals, Mumbai, India.

The disclosed compositions can be administered to a human for treating conditions including various human cancers such as colon cancer, prostate cancer, breast cancer, lung cancer, oral cancers, leukemias, etc, diabetes, depression, epilepsy, and various chronic inflammatory diseases such as rheumatoid arthritis, Alzheimer's disease, inflammatory bowel diseases (Crohn's disease, ulcerative colitis), coronary artery diseases, fibrosis and cirrhosis of liver, pancreatitis, abdominal aortic aneurysms, drug-resistant malaria, psoriasis, cystic fibrosis, HIV, wound healing, central nervous system disorders and potentially many other diseases. Another embodiment of the present invention provides for an application of a formulation of curcuminoid with essential oil of turmeric with 45% Ar-turmerone in 10:1 ratio for oral supplementation against rheumatoid arthritis and an improved method of delivering curcumin in human blood and tissues and ensuring better bioavailability in humans for the prophylaxis and treatment for active rheumatoid arthritis patients, maintenance therapy for preventing flare up of symptoms and as add on therapy with antiarthritic medications. In some embodiments, the ratio of curcuminoid mixture to essential oil of turmeric is 12:1 ratio for oral supplementation against rheumatoid arthritis and an improved method of delivering curcumin in human blood and tissues and ensuring better bioavailability in humans for the prophylaxis and treatment for active rheumatoid arthritis patients, maintenance therapy for preventing flare up of symptoms and as add on therapy with antiarthritic medications. Raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45%

Ar-turmerone in 10:1 ratio, curcuminoid with essential oil of turmeric with 10-15% Ar-turmerone in 10:1 ratio, formulation of curcuminoid with essential oil of turmeric with 45% Ar-turmerone in 10:1 ratio, curcuminoid with essential oil of turmeric with 45% Ar-turmerone in 12:1 ratio or curcuminoids 95% were given to patients with active rheumatoid arthritis for 2 months duration in a dose of 500 mg capsules twice daily. Formulation of curcuminoid with essential oil of turmeric with 45% Ar-turmerone in 10:1 and 12:1 ratios were able to significantly decrease disease activity score, total number of swollen and painful joints and erythrocyte sedimentation rate. The patients administered formulation of Curcuminoid with essential oil of turmeric with 45% Ar-turmerone in 10:1 and 12:1 ratios, also showed significant improvement when assessed according to the American College of Rheumatology criteria, functional status and pain score. The inflammatory marker C reactive protein (CRP), anti streptolysin O (ASO) values and rheumatoid arthritis factor (RA) also drastically decreased in patients taking formulation of curcuminoid with essential oil of turmeric with 45% Ar-turmerone in 10:1 and 12:1 ratios. Similar benefits were not evidenced in any of the patients given curcuminoids 95% alone in similar dose. The patients who were given maintenance therapy of formulation of curcuminoid with essential oil of turmeric with 45% Ar-turmerone in 10:1 and 12:1 ratios alone after 2 months continued to be asymptomatic during the follow up phase of 4 more months.

Another embodiment of the present invention provides for application of a formulation of curcuminoid with essential oil of turmeric with 45% Ar-turmerone in 10:1 ratio for oral supplementation against osteoarthritis and an improved method of delivering curcumin in the human blood and tissues and ensuring bioavailability in humans for the prophylaxis and treatment for osteoarthritic patients, maintenance therapy for preventing flare up of symptoms and as add on therapy with antiarthritic medications. In some embodiments, the ratio of curcuminoid mixture to essential oil of turmeric is 12:1 ratio for oral supplementation against osteoarthritis and an improved method of delivering curumin in the human blood and tissues and ensuring bioavailability in humans for the prophylaxis and treatment for osteoarthritic patients, maintenance therapy for preventing flare up of symptoms and as add on therapy with antiarthritic medications. Osteoarthritic patients were given Raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio, formulation of curcuminoid with essential oil of turmeric with 45% Ar-turmerone in 10:1 ratio. Curcuminoid with essential oil of turmeric with 45% Ar-turmerone in 12:1 ratio, and curcuminoids 95% in a dose of 500 mg twice daily for 3 months. Almost all patients in formulation of curcuminoid with essential oil of turmeric with 45% Ar-turmerone in 10:1 and 12:1 ratio group had significant improvement in the joint tenderness, crepitus, joint swelling, range of movements and gait. In the group given curcuminoids 95%, majority of patients remained symptomatic throughout the study and had to be started on analgesic drugs and antiarthritic medications before the end of the study.

Another embodiment of the present invention provides for application of formulation of curcuminoid with essential oil of turmeric with 45% Ar-turmerone in 10:1 ratio for oral supplementation in patients with Alzheimers disease and an improved method of delivering curcumin in the human blood and tissues and ensuring bioavailability in humans to delay the onset of neurodegenerative diseases like Alzheimers disease, for treatment and symptomatic improvement in patients with Alzheimers disease. In some embodiments, the ratio of curcuminoid mixture to essential oil of turmeric is 12:1 ratio for oral supplementation in patients with Alzheimers disease and an improved method of delivering curcumin in the human blood and tissues and ensuring bioavailability in humans to delay the onset of neurodegenerative diseases like Alzheimers disease, for treatment and symptomatic improvement in patients with Alzheimers disease. Alzheimers disease patients were given raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio, formulation of curcuminoid with essential oil of turmeric with 45% Ar-turmerone in 10:1 ratio, Curcuminoid with essential oil of turmeric with 45% Ar-turmerone in 12:1 ratio or curcuminoids 95% in a dose of 3 gm/day. The patients on curcuminoid with essential oil of turmeric with 45% Ar-turmerone in 10:1 and 12:1 ratio formulations significantly benefitted cognitive performance, functional impairment, behavior and global function compared with commercial curcumin formulation in the same dose. The serum level of Amyloid beta increased significantly in group taking the formulation of curcuminoid with essential oil of turmeric with 45% Ar-turmerone in 10:1 and 12:1 ratios reflecting the ability of formulation of curcuminoid with essential oil of turmeric with 45% Ar-turmerone in 10:1 and 12:1 ratios to disaggregate Amyloid beta deposits in the brain compared to curcuminoids 95%. It was also associated with an increase in the Vitamin E content between curcuminoids 95% and formulation of curcuminoid with essential oil of turmeric with 45% Ar-turmerone in 10:1 and 12:1 ratios, the values being significantly higher for the formulation of curcuminoid with essential oil of turmeric with 45% Ar-turmerone in 10:1 and 12:1 ratio groups. Another human study which supplemented formulation of curcuminoid with essential oil of turmeric with 45% Ar-turmerone in 10:1 and 12:1 ratios to patients with mild cognitive impairment over a period of 2 years showed that the risk of development of dementia and Alzheimers disease is reduced drastically in all patients on formulation of curcuminoid with essential oil of turmeric with 45% Ar-turmerone in 10:1 and 12:1 ratios therapy while majority of the patients in curcuminoids 95% progressed to dementia and 50% to Alzheimers disease within 2 years.

Another embodiment of the present invention provides for application of a formulation of curcuminoid with essential oil of turmeric with 45% Ar-turmerone in 10:1 and 12:1 ratios for oral supplementation in patients with depression and an improved method of delivering curcumin in the human blood and tissues and ensuring bioavailability in humans for treatment of patients with depression. Patients with depression were given raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio, formulation of curcuminoid with essential oil of turmeric with 45% Ar-turmerone in 10:1 ratio, curcuminoid with essential oil of turmeric with 45% Ar-turmerone in 12:1 ratio and curcuminoids 95% in a dose of 500 mg twice daily for 8 weeks. Almost all patients in formulation of curcuminoid with essential oil of turmeric with 45% Ar-turmerone in 10:1 and 12:1 ratio groups had significant reduction in the severity of depression as assessed by the Hamilton depression scale and showed significant reduction in severity of illness and improvement and response to treatment as assessed by the clinical global impression scale. The inventive compositions have the additional benefit that the essential oil components are themselves bioactive (for example, see Yue, A et al, int. J. Mol. Med., 2002, 9:481-84; Jayaprakasha, G. K. et al, Z. Naturforsch., 2002, 57:828-35) and thus are expected to synergistically enhance the bioactivity of curcumin.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

EXAMPLES

Example 1

Nine healthy human volunteers aged between 25 and 45 years of age were selected for the study. They were given capsules of curcuminoid mixture alone and capsules of enhanced curcumin capsules at the dosage of 50 mg curcuminoid/kg body weight. Enhanced curcumin is a composition having curcuminoid and added essential oil of turmeric. In the enhanced curcumin capsules the weight ratio of curcuminoid to essential oil of turmeric was 10:1. The subjects were advised to take curcuminoid capsules first. Blood samples were collected at zero hour and periodically at one-hour or half-hour intervals for 8 hours. After a washout period of one week, the same protocol was repeated with enhanced curcumin bioavailability capsules. The whole blood was extracted exhaustively with ethyl acetate to recover curcumin. The ethyl acetate extract was analyzed by HPLC on a RP-C18 column (25×4.5 mm) using tetrahydrofuran (THF) as solvent and UV detection at 420 nm. The eluant flow rate was 1 ml/min. Efficiency of the extraction procedure for recovering curcumin from blood samples was determined by measuring recovery of curcumin upon extraction of normal blood samples. Normal blood samples were collected by adding curcumin to normal blood (of persons not consuming curcumin or enhanced curcumin capsules). Curcumin was extracted from the normal blood samples by the above procedure. The efficiency of recovery of curcumin by the above extraction procedure was estimated to range between 80.12% and 86.49%.

A typical result is given in Table 1.

TABLE 1

| | Curcumin content in blood (ng/g) | |
| --- | --- | --- |
| Time (h) | Curcumin composition | Enhanced curcumin bioavailability composition |
| 0.0 | 0.0 | 0 |
| 0.5 | 3.17 | 7.85 |
| 1.0 | 7.57 | 6.23 |
| 1.5 | 4.42 | 4.84 |
| 2.0 | 13.81 | 11.95 |
| 2.5 | 9.61 | 19.22 |
| 3.0 | 5.67 | 92.59 |
| 4.0 | 8.2 | 24.33 |
| 6.0 | 1.62 | 8.43 |
| 8.0 | 1.11 | 5.09 |

The results are also graphically represented in FIG. 1. Following administration of capsules having a 10:1 weight ratio of curcuminoid to essential oil of turmeric, the peak absorption of curcumin occurred at 3 hr. Furthermore, curcumin persisted in small amounts in the blood till 8 hr beyond which measurements were not made. At peak absorption the enhancement of bioavailability ranged, among the 9 persons, between 5 and 16-fold with a mean value of 10.62.

Example 2

Human subjects were administered capsule (4×500 mg) prepared with curcuminioids and without added essential oil of turmeric (curcuminoids group in Table 2). Blood was drawn at different intervals (one hour) and tested for curcumin content. After two weeks the same groups were administered an enhanced curcumin bioavailability composition (4×500 mg). The varying ratios of curcuminoids and added essential oil of turmeric are as provided in Table 2. Blood from the enhanced curcumin group was drawn at different intervals and tested for curcumin content. As seen in Table 2, bioavailability of curcumin was greater when enhanced curcumin capsules were administered as compared to administration of capsule containing curcuminoids without added essential oil of turmeric.

TABLE 2

| Analysis of curcumin content in blood. | | |
| --- | --- | --- |
| Ratio of curcuminoids to added essential oil of turmeric | Curcumin content in blood (AUC) | |
| | Curcuminoid mixture alone group | Enhanced curcumin group |
| 90:4 | 725 | 5147.5 |
| 90:5 | 820 | 5904 |
| 90:6 | 750 | 5475 |
| 90:7 | 900 | 6300.0 |
| 90:8 | 752 | 5367.6 |
| 90.9 | 782 | 5552.2 |
| 89.9 | 696 | 5080.8 |
| 90:10 | 760 | 5320 |
| 80:9 | 726 | 5227.2 |
| 80:20 | 754 | 5315.7 |
| 90:20 | 765 | 5469.75 |
| 70:20 | 810 | 5147.5 |

The ratios of curcuminoids to added essential oil of turmeric in the enhanced curcumin bioavailability composition provided in Table 2 can also be represented as shown in Table 3. The unit of curcumin content in blood is provided as area under the curve (AUC).

TABLE 3

Ratio of curcuminoids to added essential oil in compositions for enhanced curcumin bioavailability

| Ratio of Curcuminoids to added essential oil of turmeric | Ratio of curcuminoids to added essential oil of turmeric |
|---|---|
| 90:4 | 22.5:1 |
| 90:5 | 18:1 |
| 90:6 | 15:1 |
| 90:7 | 12.9:1 |
| 90:8 | 11.25:1 |
| 90:9 | 10:1 |
| 90:10 | 9:1 |
| 80:9 | 8.9:1 |
| 80:20 | 4:1 |
| 90:20 | 4.5:1 |
| 70:20 | 3.5:1 |

Example 3

Bioavailability of Curcumin from Essential Oil of Turmeric Alone, Raw Turmeric Powder, Curcuminoid Alone, Curcuminoid with Essential Oil of Turmeric with 45% Ar-Turmerone in 10:1 Ratio and Curcuminoid with Essential Oil of Turmeric with 45% Ar-Turmerone in 12:1 Ratio Etc.

Nine healthy human volunteers were given capsules containing 475 mg of curcuminoid mixture without added essential oil of turmeric (the capsule was made up to 500 mg by addition of rice powder) at a dosage of 50 mg curcuminoid/kg body weight. Blood was drawn from the subjects at baseline, 0.5, 1, 1.5, 2, 2.5, 3, 4, 6 and 8 hours post drug. The same subjects after a washout period of one week were given 500 mg capsule having 454.55 mg curcuminoid mixture with 45.45 mg essential oil of turmeric, wherein the essential oil of turmeric had about 45% Ar-turmerone (the weight ratio of curcuminoid mixture to added essential oil of turmeric was 10:1) at a dosage of 50 mg curcuminoid/kg body weight of the subject. Blood was drawn from the subjects at baseline, 0.5, 1, 1.5, 2, 2.5, 3, 4, 6 and 8 hours post drug. Table 4 provides the amount of curcumin in nanograms per gram of blood for the subjects, which was averaged for each time point.

The above protocol was repeated with the following three formulations:
(1) A capsule having 500 mg of essential oil of turmeric, wherein the essential oil of turmeric had 10-15% Ar-turmerone, was administered at a dosage of 50 mg of essential oil of turmeric per kg body weight of the human subject;
(2) A capsule having 500 mg of essential oil of turmeric, wherein the essential oil of turmeric had 45% Ar-turmerone, administered at a dosage of 50 mg of essential oil of turmeric per kg body weight of the human subject; and
(3) A capsule having 500 mg of raw turmeric powder was administered at a dosage of 50 mg of raw turmeric powder/kg body weight of the human subject.
(4) A capsule having 500 mg of 461.5 mg curcuminoid mixture with 38.45 mg essential oil of turmeric, wherein the essential oil of turmeric had about 45% Ar-turmerone (the weight ratio of curcuminoid mixture to added essential oil of turmeric was 12:1)

Whole blood drawn from the subjects was extracted exhaustively with ethyl acetate to recover curcumin. The ethyl acetate extract was analyzed by HPLC on a RP-C18 column (25×4.5 mm) using tetrahydrofuran (THF) as solvent and UV detection at 420 nm. The eluent flow rate was 1 ml/min. As seen in Table 4 and FIG. 2, curcumin bioavailability in human subjects following administration of raw turmeric was low. Curcumin bioavailability following administration of negative controls, namely, essential oil fractions having 10-15% or 45% Ar-turmerone was not detectable (referred to as Nd in Table 4). Whereas, curcumin was detectable in human subjects following administration of curcuminoid mixture without added essential oil of turmeric, the bioavailability of curcumin was enhanced by 6.7 fold upon administration of a composition having curcuminoid mixture and essential oil of turmeric with 45% Ar-t in 10:1 ratio and the bioavailability of curcumin was enhanced by 8.3 fold upon administration of a composition having curcuminoid mixture and essential oil of turmeric with 45% Ar-t in 12:1 ratio.

Figure 2:
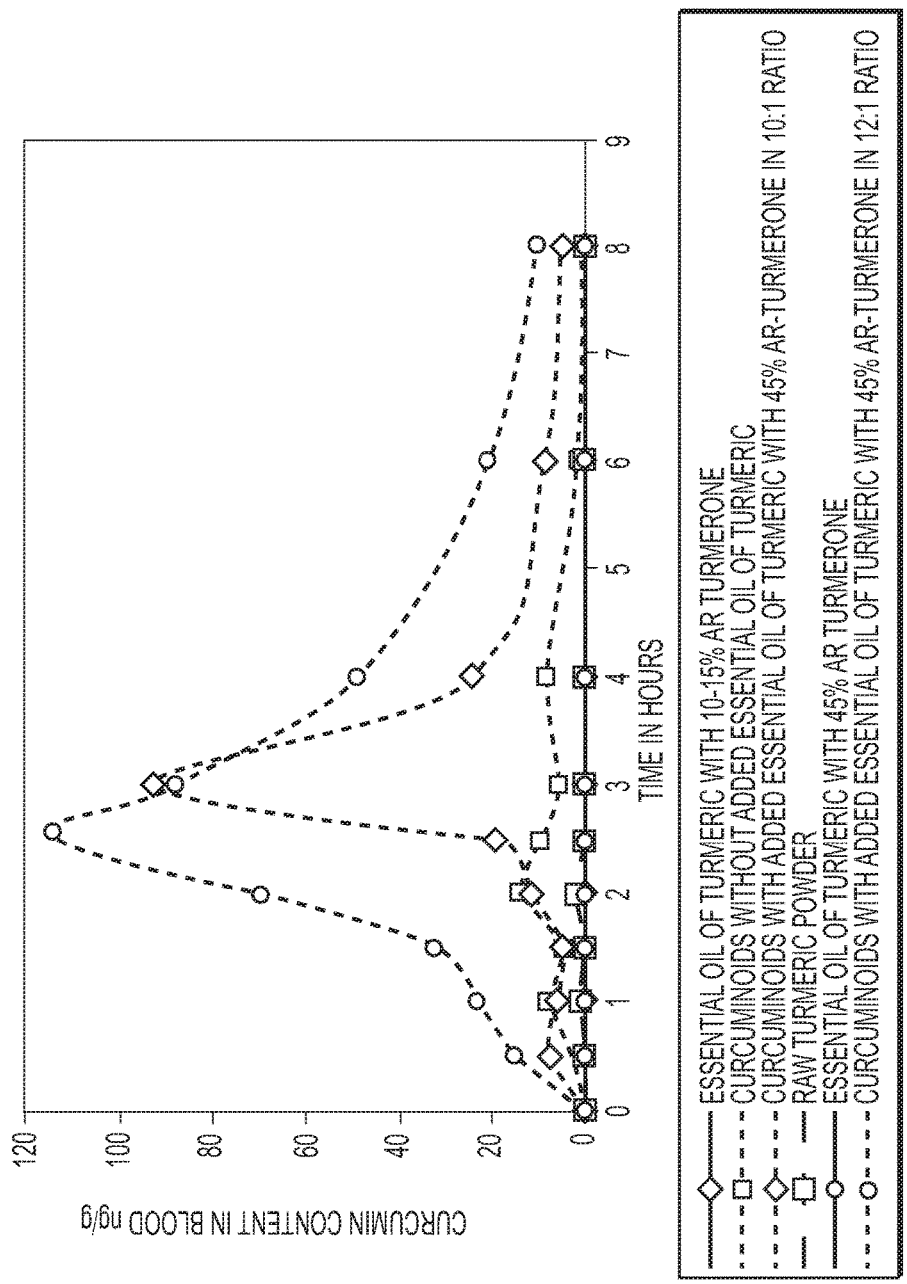

As seen in FIG. 2, the maximum concentration of curcumin in blood (Cmax of curcumin) was 13.81 ng/g upon administration of the negative control capsule having curcuminoid mixture without the added essential oil of turmeric, whereas, the Cmax of curcumin was 92.59 ng/g upon administration of the positive control capsule having curcuminoid mixture and added essential oil of turmeric with 45% Ar-t in 10:1 ratio. The Cmax of curcumin was 114.59 ng/g upon administration of the positive control capsule having curcuminoid mixture and added essential oil of turmeric with 45% Ar-t in 12:1 ratio. Therefore, comparison of the Cmax values shows that bioavailability of curcumin upon oral administration of the claimed composition having curcuminoid mixture and added essential oil of turmeric with 45% Ar-t in 10:1 was 6.7 times greater than bioavailability of curcumin upon oral administration of curcuminoid mixture without the added essential oil of turmeric. Bioavailability of curcumin upon oral administration of the claimed composition having curcuminoid mixture and added essential oil of turmeric with 45% Ar-t in 12:1 ratio was 8.3 times greater than bioavailability of curcumin upon oral administration of curcuminoid mixture without the added essential oil of turmeric.

TABLE 4

Negative and Positive Control experiments

Curcumin content: in blood (ng/g)

| Time in hours | Raw turmeric powder | Essential oil of turmeric (45% Ar-turmerone) | Essential oil of turmeric (10-15% Ar-turmerone) | Curcuminoid mixture without added Essential oil of turmeric | Curcuminoid mixture with added essential oil of turmeric (45% Ar-turmerone) 10:1 | Curcuminoid mixture with added essential oil of turmeric (45% Ar-turmerone) 12:1 |
|---|---|---|---|---|---|---|
| 0 | 0 | 0 | 0 | 0 | 0 | 0 |
| 0.5 | Nd | Nd | Nd | 3.17 | 7.85 | 15.2 |

TABLE 4-continued

Negative and Positive Control experiments

Curcumin content: in blood (ng/g)

| Time in hours | Raw turmeric powder | Essential oil of turmeric (45% Ar-turmerone) | Essential oil of turmeric (10-15% Ar-turmerone) | Curcuminoid mixture without added Essential oil of turmeric | Curcuminoid mixture with added essential oil of turmeric (45% Ar-turmerone) 10:1 | Curcuminoid mixture with added essential oil of turmeric (45% Ar-turmerone) 12:1 |
|---|---|---|---|---|---|---|
| 1 | 1.05 | Nd | Nd | 7.57 | 6.23 | 23.4 |
| 1.5 | Nd | Nd | Nd | 4.42 | 4.84 | 32.8 |
| 2 | 2.1 | Nd | Nd | 13.81 | 11.95 | 69.8 |
| 2.5 | Nd | Nd | Nd | 9.61 | 19.22 | 114.59 |
| 3 | Nd | Nd | Nd | 5.67 | 92.59 | 88.5 |
| 4 | Nd | Nd | Nd | 8.2 | 24.33 | 49.4 |
| 6 | Nd | Nd | Nd | 1.62 | 8.43 | 20.74 |
| 8 | Nd | Nd | Nd | 1.11 | 5.09 | 10.8 |

Example 4

Bioavailability of Curcumin from Capsules Having a Weight Ratio of Curcuminoid Mixture to Essential Oil of Turmeric Ranging from about 1:3 to 99:1

Human volunteers aged between 25 and 45 years were randomized into separate groups having 3 subjects each (Groups A through W). For control experiment, at the initial time point, subjects in all the groups were four 500 mg capsules of C without added E having about 475 mg of curcuminoid mixture. Then blood was drawn from the subjects at different time periods (0.5, 1, 1.5, 2, 2.5, 3, 4, 6 and 8 hours post drug) and the amount of curcumin in blood (in nanograms per gram of blood) was determined. The average values of curcumin in blood at each time period was plotted in separate graphs for each of the groups (A to W). For each of the groups, the area under the curve (AUC) of curcumin was calculated from the figure. In Table 5 and FIG. 3, AUC is provided as nanograms of curcumin per gram of blood.

After a wash out period of 2 weeks, subjects in groups A through W were given four 500 mg capsules each, wherein set of 4 capsules had varying ratios of curcuminoid mixture to added essential oil of turmeric (referred to as C with added E capsule in Table 5), and wherein the essential oil of turmeric in the capsules had 45% Ar-turmerone. The ratio of curcuminoid mixture to essential oil of turmeric in the capsules ranged from about 99:1 to about 1:3. Some of the could be expressed as more than one type of ratio, for example, as 95:5 or 19:1; 90:4 or 22.5:1; 90:5 or 18:1; 90:6 or 15:1; 90:7 or 12.9:1; 90:8 or 11.3:1; 90:9 or 10:1; 90:10 or 9:1; 90:20 or 4.5:1; 89:9 or 9.8:1; 80:9 or 8.8:1; 80:20 or 4:1; 70:20 or 3.5:1; 75:25 or 3:1; 60:30 or 2:1; 50:50 or 1:1, 30:60 or 1:2 and 25:75 or 1:3 and therefore the ratios are referred to accordingly in Table 5.

As shown in Table 5, each of the groups was administered a capsule having a different weight ratio of curcuminoid mixture to essential oil of turmeric (referred to as C:E). Blood was drawn from the subjects and the AUC was calculated as described above. The curcumin content in the blood for each group was expressed as AUC, which was used to compare the bioavailability of curcumin from the different treatment groups.

Figure 3:
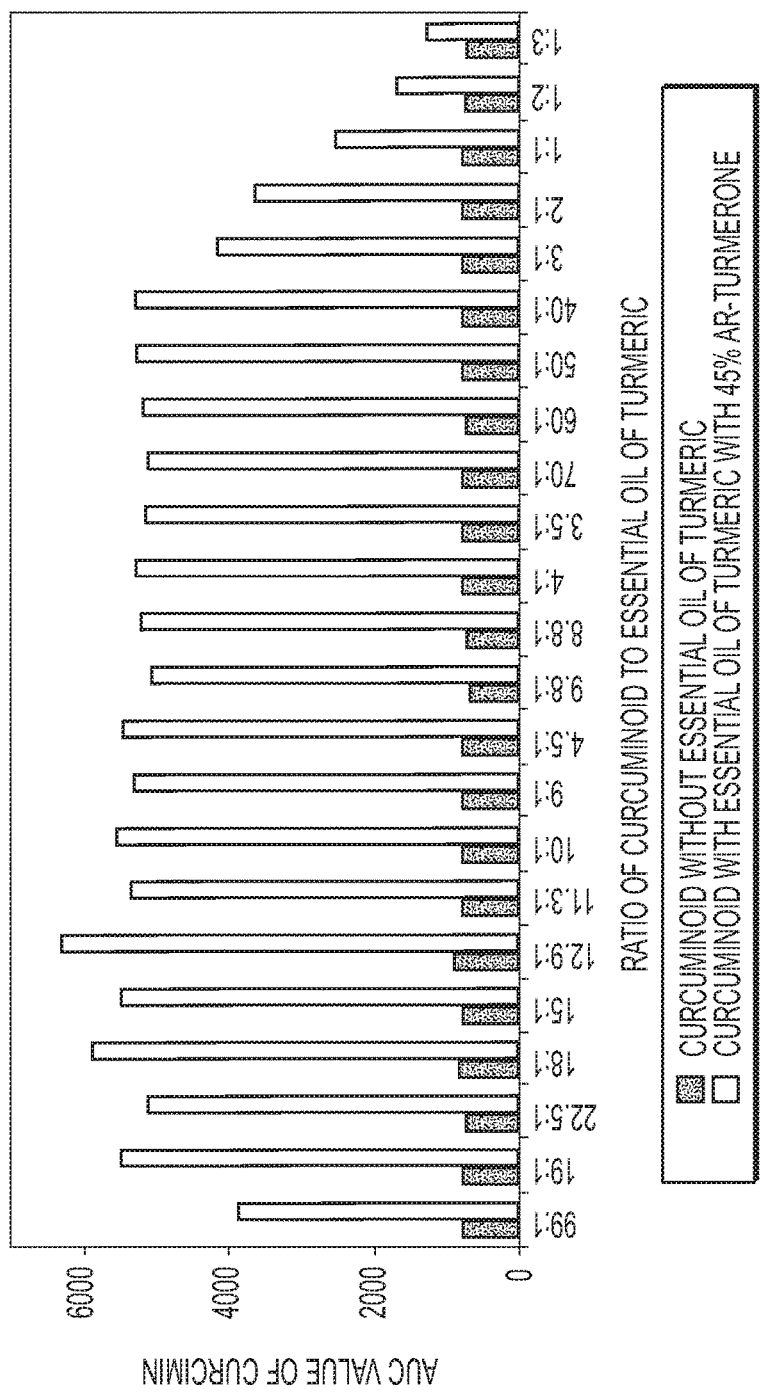

Table 5 and FIG. 3 provide a comparison of the bioavailability of curcumin from the curcuminoid mixture without added essential oil of turmeric as the control group and the curcuminoid mixture with added essential oil of turmeric with 45% Ar-turmerone.

As seen in Table 5 and FIG. 3, curcumin bioavailability upon administration of capsules having curcuminoid mixture with added essential oil of turmeric with 45% Ar-turmerone resulted in an enhancement of bioavailability ranging from 1.8 to 7.3 fold over the curcumin bioavailability that was observed when negative control capsules having curcuminoid mixture without added essential oil of turmeric were administered. The results in Table 5 further show that the enhancement of bioavailability was observed over the entire claimed range of the ratio about 1:3 to about 99:1 of curcuminoid mixture to essential oil of turmeric.

TABLE 5

Bioavailability of curcumin from compositions having weight ratios of curcuminoid mixture to added essential oil of turmeric ranging from 1:3 to 99:1

| | | | C without added E | | C with added E | | |
|---|---|---|---|---|---|---|---|
| Group | Ratio of C:E | Dosage 4 caps each | C (mg) per capsule | C (ng) per gm of blood (AUC) | C (mg) per capsule | E (mg) per capsule | C (ng) per gm of blood (AUC) |
| A | 99:1 | 500 mg | 475 | 771 | 495 | 5 | 3855 |
| B | 95:5 or 19:1 | 500 mg | 475 | 786 | 475 | 25 | 5515 |
| C | 90:4 or 22.5:1 | 500 mg | 475 | 725 | 478.72 | 21.28 | 5147.5 |
| D | 90:5 or 18:1 | 500 mg | 475 | 820 | 473.68 | 26.32 | 5904 |
| E | 90:6 or 15:1 | 500 mg | 475 | 750 | 468.75 | 31.25 | 5475 |

TABLE 5-continued

Bioavailability of curcumin from compositions having weight ratios of curcuminoid mixture to added essential oil of turmeric ranging from 1:3 to 99:1

| | | | C without added E | | C with added E | | |
|---|---|---|---|---|---|---|---|
| Group | Ratio of C:E | Dosage 4 caps each | C (mg) per capsule | C (ng) per gm of blood (AUC) | C (mg) per capsule | E (mg) per capsule | C (ng) per gm of blood (AUC) |
| F | 90:7 or 12.9:1 | 500 mg | 475 | 900 | 463.77 | 36.23 | 6300 |
| G | 90:8 or 11.3:1 | 500 mg | 475 | 752 | 459.35 | 40.65 | 5367.6 |
| H | 90:9 or 10:1 | 500 mg | 475 | 782 | 454.55 | 45.45 | 5552.2 |
| I | 90:10 or 9:1 | 500 mg | 475 | 760 | 450 | 50 | 5320 |
| J | 90:20 or 4.5:1 | 500 mg | 475 | 765 | 409.1 | 90.9 | 5469.75 |
| K | 89:9 or 9.8:1 | 500 mg | 475 | 696 | 453.7 | 46.3 | 5080.8 |
| L | 80:9 or 8.8:1 | 500 mg | 475 | 726 | 448.98 | 51.02 | 5227.2 |
| M | 80:20 or 4:1 | 500 mg | 475 | 754 | 400 | 100 | 5315.7 |
| N | 70:20 or 3.5:1 | 500 mg | 475 | 810 | 388.89 | 111.11 | 5147.5 |
| O | 70:1 | 500 mg | 475 | 769 | 493 | 7 | 5124 |
| P | 60:1 | 500 mg | 475 | 725 | 491.8 | 8.2 | 5200 |
| Q | 50:1 | 500 mg | 475 | 749 | 490.2 | 9.8 | 5284 |
| R | 40:1 | 500 mg | 475 | 737 | 487.8 | 12.2 | 5310 |
| S | 75:25 or 3:1 | 500 mg | 475 | 756 | 375 | 125 | 4158 |
| T | 60:30 or 2:1 | 500 mg | 475 | 742 | 333.3 | 166.6 | 3635.8 |
| U | 50:50 or 1:1 | 500 mg | 475 | 788 | 250 | 250 | 2537 |
| V | 30:60 or 1:2 | 500 mg | 475 | 715 | 166.6 | 333.3 | 1651 |
| W | 25:75 or 1:3 | 500 mg | 475 | 726 | 125 | 375 | 1276 |

Example 5

Comparison of Curcumin Bioavailability from 10:1 and 1:10 Weight Ratios of Curcuminoid Mixture to Essential Oil of Turmeric Nine healthy human volunteers were given four 500 mg capsules having 20 mg curcuminoid mixture without added essential oil of turmeric (referred to as 20 mg C in Table 6). Blood was drawn from the subjects at baseline, 0.5, 1, 1.5, 2, 2.5, 3, 4, 6 and 8 hours post drug. Following one week washout period, the same nine subjects were given four 500 mg capsules having 200 mg of essential oil of turmeric having 10 to 15% Ar-turmerone. Blood was drawn from the subjects at baseline, 0.5, 1, 1.5, 2, 2.5, 3, 4, 6 and 8 hours post drug.

With one week washout period between treatments, the subjects were tested for the following treatments, wherein four of 500 mg capsules were administered to each subject. If any of the capsules had less than 500 mg of the test component such as curcuminoid mixture or essential oil or the combination of curcuminoid mixture and essential oil, then the capsules were made up to 500 mg by addition of a placebo, e.g. rice powder. In one treatment, each capsule had a 1:10 ratio of curcuminoid mixture to added essential oil of turmeric. Each capsule contained 20 mg curcuminoid and 200 mg essential oil of turmeric, wherein the essential oil of turmeric had 10 to 15% Ar-turmerone (referred to as Ar-t in Table 6).

In another treatment, each capsule had a 1:10 ratio of curcuminoid mixture to added essential oil of turmeric, wherein the essential oil had 45% Ar-turmerone. Each capsule contained 20 mg curcuminoid and 200 mg essential oil of turmeric. The capsule is referred to as 20 mg C: 200 mg E=1:10 (E had 10-15% Ar-t) in Table 6.

In another treatment, the capsule had a 10:1 ratio of curcuminoid mixture to added essential oil of turmeric, wherein the essential oil had 45% Ar-turmerone. Each capsule contained 20 mg curcuminoid and 2 mg essential oil of turmeric. The capsule is referred to as 20 mg C: 2 mg E=10:1 (E had 45% Ar-t) in Table 6.

In another treatment, each capsule had curcuminoid mixture without the added essential oil of turmeric. Each capsule contained 454.55 mg curcuminoids. The capsule is referred to as 454.55 mg C without added E in Table 6.

In another treatment, each capsule had essential oil of turmeric having 45% Ar-turmerone. Each capsule contained 45.45 mg essential oil of turmeric. The capsule is referred to as 45.45 mg E (45% Ar-t) in Table 6.

In another treatment, each capsule had curcuminoid mixture along with added essential oil of turmeric with 45% Ar-turmerone at a 10:1 ratio. Each capsule contained 454.55 mg curcuminoids and 45.45 mg of essential oil of turmeric. The essential oil of turmeric had 45% Ar-turmerone. The capsule is referred to as 454.55 mg C: 45.45 mg E=10:1 (E had 45% Ar-t) in Table 6.

Figure 4:
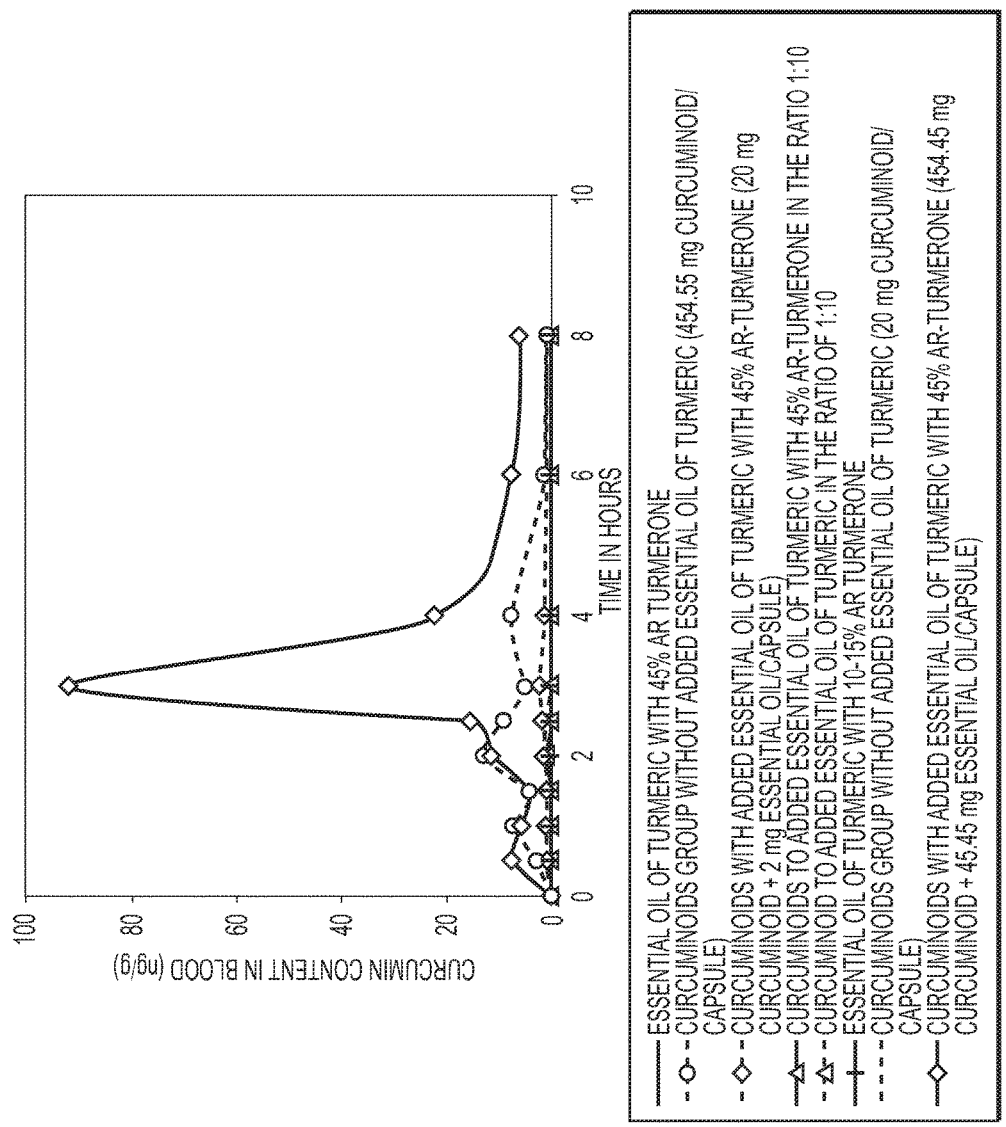

Whole blood from the subjects was extracted exhaustively with ethyl acetate to recover curcumin. The ethyl acetate extract was analyzed by HPLC on a RP-C18 column (25×4.5 mm) using tetrahydrofuran (THF) as solvent and UV detection at 420 nm. The eluent flow rate was 1 ml/min. Curcumin content in the blood was determined for each group at each time point and the average value of curcumin in blood (in nanogram per gram of blood) was calculated. The average value of curcumin at each time point for various the treatment protocols is provided in Table 6 and in FIG. 4.

As seen in Table 6, low bioavailability of curcumin of about 1.05 ng curcumin per gm of blood was observed from the negative control having 20 mg of curcuminoid mixture without added essential oil of turmeric. In the negative controls having essential oil of turmeric alone, with either 10-15% Ar-turmerone or 45% Ar-turmerone, the bioavailability of curcumin was not detectable (referred to as Nd in Table 6). Further, bioavailability of curcumin from the capsule prepared and having a 1:10 ratio of curcuminoid mixture to essential oil of turmeric, wherein the essential oil had either a 10-15% Ar-turmerone content or 45% Ar-turmerone content, showed poor bioavailability of curcumin.

An experimental capsule prepared at the ratio of 10:1 of curcuminoid mixture to essential oil of turmeric, wherein the essential oil had a 45% Ar-turmerone content, having 20 mg curcuminoid mixture and 2 mg essential oil of turmeric showed greater than 2-told enhanced bioavailability over the negative control of 20 mg curcuminoid mixture without the added essential oil of turmeric. On the other hand the positive control having 454.55 mg curcuminoid mixture and 45.55 mg essential oil of turmeric, wherein the essential oil of turmeric had a 45% Ar-turmerone content, i.e., a 10:1 ratio of curcuminoid mixture to essential oil of turmeric, showed a 6.97 fold enhancement of bioavailability of curcumin as compared to the bioavailability of curcumin from the negative control capsule having 454.55 mg curcuminoid mixture without the added essential oil of turmeric.

TABLE 6

Comparison of curcumin bioavailability from 10:1 and 1:10 weight ratios of curcuminoid mixture to essential oil of turmeric

| | | Nanograms of curcumin per gram of blood | | | | | | |
|---|---|---|---|---|---|---|---|---|
| Time (h) | 20 mg C | 200 mg E alone (10-15% Ar-t) | 20 mg C:200 mg E = 1:10 (E had 10-15% Ar-t) | 20 mg C:200 mg E = 1:10 (E had 45% Ar-t) | 20 mg C:2 mg E = 10:1, (E had 45% Ar-t) | 454.55 mg C without added E | 45.45 mg E (45% Ar-t) | 454.55 mg C:45.45 mg E = 10:1 (E had 45% Ar-t) |
| 0 | 0 | 0 | 0 | 0 | 0 | 0 | 0 | 0 |
| 0.5 | Nd | Nd | Nd | Nd | 1.1 | 3.02 | Nd | 7.45 |
| 1 | Nd | Nd | Nd | Nd | 1 | 7.27 | Nd | 5.81 |
| 1.5 | Nd | Nd | Nd | Nd | 1.05 | 4.11 | Nd | 4.52 |
| 2 | 1.05 | Nd | 1.1 | 1.3 | 1.3 | 13.18 | Nd | 11.46 |
| 2.5 | Nd | Nd | Nd | 1.1 | 1.7 | 9.17 | Nd | 15.66 |
| 3 | Nd | Nd | Nd | Nd | 2.67 | 5.21 | Nd | 91.9 |
| 4 | Nd | Nd | Nd | Nd | 1.34 | 7.82 | Nd | 22.44 |
| 6 | Nd | Nd | Nd | Nd | 1.1 | 1.54 | Nd | 8.01 |
| 8 | Nd | Nd | Nd | Nd | 1.05 | 1.05 | Nd | 6.18 |

Example 6

Method of Preparation of Curcuminoid Mixture with 95% Curcuminoids

The rhizomes of turmeric (300 Kg) were dried. The dried turmeric rhizomes were powdered to form powdered turmeric. The powdered turmeric was treated with ethyl acetate (900 L) to form a solution. The extraction was carried out at 78° C. temperature for 1 hr. After initial extraction, the extraction process was repeated 4 more times and the resultant solution was filtered and the solvent was stripped from the filtered solution to form an extract. This extract was cooled to about 4° C. to obtain crystals of curcuminoid (12 Kg) and a liquid. The crystals of curcuminoid were isolated from the liquid by filtration. The crystals were powdered to form powdered curcuminoid mixture with 95% curcuminoids.

Example 7

Method of Preparation of Curcuminoid Mixture with 24% Curcuminoids

The rhizomes of turmeric (50 Kg) were dried and flaked into required size. The flakes of turmeric was filled in the soxhlect apparatus and extracted with ethylene dichloride (EDC). The extraction was carried out for 5 hrs at a temperature of about 83° C. After the completion of extraction, the solvent was filtered. The solvent was removed by distillation and mild vacuum was applied to get an oleoresin which contains essential oil of turmeric and curcuminoid. The oleoresin was steam distilled to get essential oil and a residue. The residue was dried under vacuum to form a powder (10 Kg) with 24% curcuminoid content.

Example 8

Method of Analysis of Total Curcuminoids by HPLC Method

From 500 mg capsule, 25 mg was accurately weighed and transferred into a 50 ml standard flask and made up to a 50 ml solution with methanol. From this pipette out 2 ml into 50 ml standard flask and made up to a 50 ml solution with methanol. Filter through 0.2 µm membrane filter before injection. Standard was prepared by weighing accurately 25 mg standard [Curcumin Standard: ~99% Total Curcuminoids (Sigma)] and transferred into a 50 ml standard flask and made up to a 50 ml solution with methanol. From this pipette out 2 ml into 50 ml standard flask and made up to a 50 ml solution with methanol. Filter through 0.2 µm membrane filter before injection.

The total Curcuminoids was analyzed by high performance liquid chromatography (HPLC) on a C18 column ((250×4.6 mm Shimadzu Co., Japan.) using tetrahydrofuran (THF) as the mobile phase and UV detection at 420 nm. The eluent flow rate was 1 ml/min.

By comparing the area of standard and sample, the percentage of total curcuminoids was calculated using the formula $$\% \text{ of total Curcuminoid} = \frac{\text{Area of sample} \times \text{amount of std} \times \text{Purity of } std}{\text{Area of } Std \times \text{weight of the sample}}$$

Example 9

Method of Preparation of Essential Oil of Turmeric with Varying Concentration of Ar-Turmerone The rhizomes of turmeric (500 Kg) were dried. The dried turmeric rhizomes were powdered to form powdered turmeric. The powdered turmeric was treated with ethyl acetate (1500 L) to form a solution. The extraction was carried out at 78° C. temperature for 1 hr. After initial extraction, the extraction process was repeated 4 more times and the resultant solution was filtered and the solvent was stripped from the filtered solution to form an extract. This extract was cooled to about 4° C. to obtain crystals of curcuminoid (20 Kg) and a liquid. The crystals of curcuminoid were isolated from the liquid by filtration.

Figure 5:
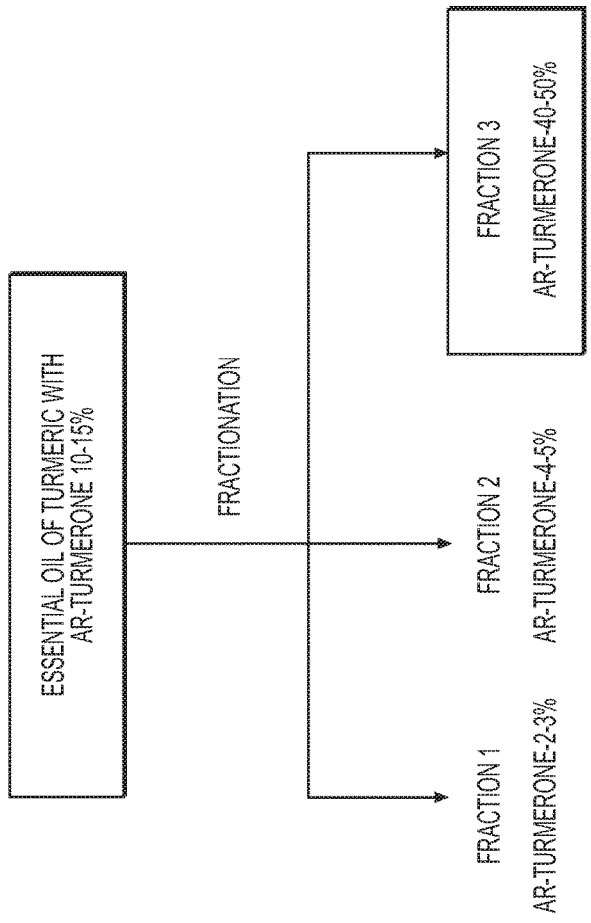

The remaining liquid comprises the essential oil of turmeric and a resin. The liquid was then steam distilled to isolate essential oil of turmeric with 10-15% Ar turmerone (25 Kg). After fractionating this oil, essential oil with 45% Ar turmerone (7.5 Kg) was obtained as fraction 3, essential oil of turmeric with 4-5% Ar turmerone (8.3) was obtained as fraction 2 and essential oil of turmeric with 2-3% Ar turmerone (9.3 Kg) was obtained as fraction 1. (FIG. 5)

Example 10

Method of Preparation of Combination of Curcuminoids and Essential Oil of Turmeric with 45% Ar Turmerone in 10:1 Ratio The curcuminoid powder prepared as per Example 6 (2.7 Kg) was suspended in water (12 L) to form a suspension. Fraction of essential oil containing 45% Ar-turmerone prepared as per Example 9 (0.27 Kg) was added to the suspension in 10:1 ratio. The mixture is pulverized in a colloidal mill to form fine slurry. Water is stripped from the slurry under heat and vacuum to form a uniform blend. (3 Kg).

A 500 mg capsule containing 454.55 mg of curcuminoid and 45.45 mg of Essential oil with 45% Ar-turmerone in a weight ratio of about 90:9 (10:1) was prepared by encapsulating the above blended extract powder in hard gelatin capsules done in an air-conditioned at 21° C. and de-humidified room. 3 kg of extract powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 6000 capsules of 500 mg each.

Example 11

Method of Preparation of Combination of Curcuminoids and Essential Oil of Turmeric with 45% Ar-Turmerone in 1:10 Ratio The powdered curcuminoid mixture prepared as per Example 6 (0.27 Kg) was suspended in water (1 L) to form a suspension. Fraction of essential oil of turmeric containing 45% Ar-turmerone prepared as per Example 9 (2.7 Kg) was added to the suspension in 1:10 ratio. The mixture is pulverized in a colloidal mill to form fine slurry. Water was stripped from the slurry under heat and vacuum to form a uniform blend (3 Kg).

Capsule containing curcuminoid and Essential oil of turmeric with 45% Ar-turmerone in a weight ratio of about 1:10 was prepared by encapsulating the above blended extract powder in soft gelatin capsules done in an air-conditioned at 21° C. and de-humidified room. 3 kg of extract powder was charged into the hopper of a semi-automatic capsule filling machine. '0' size soft gelatin capsule shell was loaded to the tray and the blended extract powder was filled into the shell. The filled weights of capsules were checked simultaneously and these capsules were sorted by a sorting machine and polished with the help of a polishing machine.

Example 12

Method of Preparation of Combination of Curcuminoids and Essential Oil of Turmeric with 45% Ar Turmerone in 1:1 Ratio The powdered curcuminoid mixture prepared as per Example 6 (1.5 Kg) was suspended in water (6 L) to form a suspension. Fraction of essential oil of turmeric containing 45% Ar-turmerone prepared as per Example 9 (1.5 Kg) was added to the suspension in 1:1 ratio. The mixture was pulverized in a colloidal mill to form fine slurry. Water was stripped from the slurry under heat and vacuum to form a uniform blend. (3 Kg).

A 500 mg capsule containing 250 mg of curcuminoid and 250 mg of Essential oil of turmeric with 45% Ar-turmerone in a weight ratio of about 1:1 was prepared by encapsulating the above blended extract powder in hard gelatin capsules done in an air-conditioned at 21° C. and de-humidified room. 3 kg of extract powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 6000 capsules of 500 mg each.

Example 13

Method of Preparation of Combination of Curcuminoids and Essential Oil of Turmeric with 10-15% Ar Turmerone in 10:1 Ratio The powdered curcuminoid mixture prepared as per Example 6 (2.7 Kg) was suspended in water (12 L) to form a suspension. Fraction of essential oil of turmeric containing 10-15% Ar-turmerone prepared as per Example 9 (0.27 Kg) was added to the suspension in 10:1 ratio. The mixture was pulverized in a colloidal mill to form fine slurry. Water was stripped from the slurry under heat and vacuum to form a uniform blend (3 Kg).

A 500 mg capsule containing 454.55 mg of curcuminoid and 45.45 mg of Essential oil of turmeric with 10-15% Ar-turmerone in a weight ratio of about 90:9 (10:1) was prepared by encapsulating the above blended extract powder in hard gelatin capsules done in an air-conditioned at 21° C. and de-humidified room. 3 kg of extract powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 6000 capsules of 500 mg each.

Example 14

Method of Preparation of Capsules Containing Essential Oil of Turmeric with 45% Ar-Turmerone A 500 mg capsule with essential oil of turmeric containing 45% Ar-turmerone was prepared by encapsulating the essential oil of turmeric with 45% Ar-turmerone prepared as per example 9 (2.5 kg) in soft gelatin capsules done in an air-conditioned at 21° C. and de-humidified room. 2.5 kg essential oil of turmeric with 45% Ar-turmerone was charged into the hopper of a semi-automatic capsule filling machine. '0' size soft gelatin capsule shell was loaded to the tray and the blended extract powder was filled into the shell. The filled weight of capsules were checked simultaneously and these capsules were sorted by a sorting machine and polished with the help of a polishing machine to give 5000 capsules of 500 mg each.

Example 15

Method of Preparation of Capsules Containing Essential Oil of Turmeric with 10-15% Ar-Turmerone A 500 mg capsule with essential oil of turmeric containing 10-15% Ar-turmerone was prepared by encapsulating the essential oil with 10-15% Ar-turmerone prepared as per example 9 (2.5 kg) in soft gelatin capsules done in an air-conditioned at 21° C. and de-humidified room. 2.5 kg essential oil of turmeric with 10-15% Ar-turmerone was charged into the hopper of a semi-automatic capsule filling machine. '0' size soft gelatin capsule shell was loaded to the tray and the blended extract powder was filled into the shell. The filled weight of capsules were checked simultaneously and these capsules were sorted by a sorting machine and polished with the help of a polishing machine to give 5000 capsules of 500 mg each.

Example 16

Method of Preparation of Capsules Containing Curcuminoids 95%

A 500 mg capsule containing curcuminoids 95% was prepared by encapsulating the curcuminoid powder with 95% curcuminoids in hard gelatin capsules done in an air-conditioned at 21° C. and de-humidified room. 3 kg of powder was charged into the hopper of a semi-automatic capsule filling machine. '0' size hard gelatin capsule shell was loaded to the tray and the powder was filled into the shell. The filled weight of capsules were checked simultaneously and these capsules were sorted by a sorting machine and polished with the help of a polishing machine to give 6000 capsules of 500 mg each.

Example 17

Method of Preparation of Combination of Curcuminoids with 24% Curcuminoids and Essential Oil of Turmeric with 45% Ar-Turmerone in 10:1 Ratio The powdered curcuminoid prepared as per Example 7 (2.7 Kg) was suspended in water (12 L) to form a suspension. Fraction of essential oil containing 45% Ar-turmerone prepared as per Example 9 (0.27 Kg) was added to the suspension in 10:1 ratio. The mixture was pulverized in a colloidal mill to form fine slurry. Water was stripped from the slurry under heat and vacuum to form a uniform blend (3 Kg).

A 500 mg capsule containing 454.55 mg of curcuminoid and 45.45 mg of Essential oil with 45% Ar-turmerone in a weight ratio of about 90:9 (10:1) was prepared by encapsulating the above blended extract powder in hard gelatin capsules done in an air-conditioned at 21° C. and de-humidified room. 3 kg of extract powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 6000 capsules of 500 mg each.

Example 18

Method of Preparation of Raw Turmeric Powder

The raw turmeric rhizomes (10 Kg) were collected and cleaned. The rhizomes were dried and pulverized to get turmeric powder (2.5 Kg). The turmeric powder was sieved through 20 meshes. A 500 mg capsule with raw turmeric powder (curcuminoids 5%) was prepared by encapsulating the powder in hard gelatin capsules done in an air-conditioned at 21° C. and de-humidified room. 2.5 kg raw turmeric powder is charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 5000 capsules of 500 mg each.

Example 19

Method of Preparation of Combination of Curcuminoids and Essential Oil of Turmeric with 45% Ar Turmerone in 12:1 Ratio The curcuminoid powder prepared as per Example 6 (3.5 Kg) was suspended in water (15 L) to form a suspension. Fraction of essential oil containing 45% Ar-turmerone prepared as per Example 9 (0.29 Kg) was added to the suspension in 12:1 ratio. The mixture is pulverized in a colloidal mill to form fine slurry. Water is stripped from the slurry under heat and vacuum to form a uniform blend. (3.8 Kg).

A 500 mg capsule containing 461.5 mg of curcuminoid and 38.45 mg of Essential oil with 45% Ar-turmerone in a weight ratio of about 12:1 (curcumin 69.5%, demethoxy curcumin 17% and bisdemethoxy curcumin 4% and Essential oil of turmeric 7.5%) was prepared by encapsulating the above blended extract powder in hard gelatin capsules done in an air-conditioned at 21° C. and de-humidified room. 3 kg of extract powder was charged into the hopper of a semi-automatic capsule filling machine. '0' size hard gelatin capsule shell was loaded to the tray and the blended extract powder was filled into the shell. The filled weight of capsules were checked simultaneously and these capsules were sorted by a sorting machine and polished with the help of a polishing machine to give 6000 capsules of 500 mg each.

Example 20

Human Clinical Study of Different Turmeric Extracts in Patients with Rheumatoid Arthritis In a human clinical study to assess the efficacy of formulation of curcuminoid with essential oil of turmeric with 45% Ar-turmerone in 10:1 ratio compared to raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio, Curcuminoid with essential oil of turmeric with 45% Ar-turmerone in 12:1 ratio, and curcuminoids 95% in patients with rheumatoid arthritis, 50 patients diagnosed with rheumatoid arthritis were randomized into 10 groups viz., Group1: Subjects receiving raw turmeric powder 500 mg capsules prepared as described in Example 18 twice daily
Group2: Subjects receiving essential oil of turmeric with 45% Ar-turmerone (EOT with 45% Ar-t) 500 mg capsules prepared as described in Example 14 twice daily Group3: Subjects receiving essential oil of turmeric with 10-15% Ar-turmerone (EOT with 10-15% Ar-t) 500 mg capsules prepared as described in Example 15 twice daily Group4: Subjects receiving curcuminoid with essential oil of turmeric with 45% Ar-turmerone in 1:10 ratio (C+E with 45% Ar-t in 1:10 ratio), 500 mg capsules prepared as described in Example 11 twice daily.

Group5: Subjects receiving curcuminoid with essential oil of turmeric with 45% Ar-turmerone in 1:1 ratio (C+E with 45% Ar-t in 1:1 ratio), 500 mg capsules prepared as described in Example 12 twice daily Group6: Subjects receiving curcuminoid 24% with essential oil of turmeric with 45% Ar-turmerone in 10:1 ratio (C 24%+E with 45% Ar-t in 10:1 ratio), 500 mg capsules prepared as described in Example 17 twice daily.

Group7: Subjects receiving curcuminoid with essential oil of turmeric with 10-15% Ar-turmerone in 10:1 ratio (C+E with 10-15% Ar-t in 10:1 ratio), 500 mg capsules prepared as described in Example 13 twice daily Group8: Subjects receiving curcuminoids 95% 500 mg capsules prepared as described in Example 16, twice daily.

Group9: Subjects receiving formulation of curcuminoid with essential oil of turmeric with 45% Ar-turmerone in 10:1 ratio (C+E with 45% Ar-t in 10:1 ratio) 500 mg capsules prepared as described in Example 10, twice daily dose after food with water for a period of 8 weeks.

Group10: Subjects receiving formulation of curcuminoid with essential oil of turmeric with 45% Ar-turmerone in 12:1 ratio (C+E with 45% Ar-t in 12:1 ratio) 500 mg capsules prepared as described in Example 19, twice daily dose after food with water for a period of 8 weeks.

Subjects aged 18-65 years of either sex diagnosed to have rheumatoid arthritis (RA) according to the revised 1987 ACR criteria for the classification of rheumatoid arthritis Class I or II, with Disease Activity Score (DAS)>5, receiving treatment on an outpatient basis were included in the study. Patients with inflammatory joint disease other than RA and having concurrent treatment with any NSAID, DMARD or any anti-TNF-α therapy or other anti arthritic therapy were excluded. The study examinations included general and clinical examination, evaluation of disease, recording of vital signs, X-ray AP view of chest/hands/wrist/foot, ECG, Haematology, Blood chemistry and Urine Pregnancy Test for women of child bearing potential.

Efficacy and safety evaluations were performed at biweekly intervals. Patients were assessed for the primary efficacy endpoints disease activity score (DAS) 28 and ACR criteria. DAS is the numerical sum of four outcome parameters: tender and swollen joint count (28-joint assessment), patient's global assessment of disease on a visual analog scale (VAS; 0, no pain and 100, severe pain); and erythrocyte sedimentation rate. The ACR criteria are indicated as ACR 20, ACR 50, and ACR 70. ACR criteria measures improvement in tender or swollen joint counts and improvement in three of the following five parameters: patient global assessment—global assessment of disease activity on a 0-100 scale (0, best; 100, worst); physician assessment—global assessment of disease activity on a 0-100 scale (0, best; 100, worst); pain scale disability—visual analogue scale for pain (VAS; 0, no pain and 100, severe pain); functional questionnaire—HAQ (Health Assessment Questionnaire) includes four categories: dressing and grooming, arising, eating, and walking, on a 0-3 scale (0, best: 3, worst); acute phase reactant (such as sedimentation rate). ACR20 is defined as a reduction in tender and swollen joint counts of 20%, ACR 50 of 50% and ACR 70 of 70%, from baseline. Monitoring of vital signs, physical examinations, laboratory parameters (hematology, blood chemistry, C-reactive protein (CRP), antistreptolysin-O (ASO), rheumatoid factor and blood sugar) were performed biweekly for safety evaluation. The occurrence of adverse events was the primary safety variable.

Treatment with formulation of curcuminoid with essential oil of turmeric with 45% Ar-turmerone in 12:1 ratio showed decrease in disease activity score from 6.5 at baseline to 3 at the end of treatment.

Treatment with formulation of curcuminoid with essential oil of turmeric with 45% Ar-turmerone in 10:1 ratio showed decrease in disease activity score from 6.5 at baseline to 3.5 at the end of treatment. The results are summarized in Table 7. Mean VAS scores for pain in all the groups were comparable at baseline, and formulation of curcuminoid with essential oil of turmeric with 45% Ar-turmerone in 10:1 ratio group showed significant reduction (65%) in VAS score from 79 mm at baseline to 27.5 mm at the end of treatment. Mean VAS scores for pain in the group with formulation of curcuminoid with essential oil of turmeric with 45% Ar-turmerone in 12:1 ratio group also showed significant reduction (69%) in VAS score from 78 mm at baseline to 24 mm at the end of treatment. The results are summarized in Table 8. All components of ACR response criteria viz., Total Painful Joints, Total Swollen Joints. Patient's GA, Physician's GA, Disability Index and HAQ showed a significant reduction from baseline to end of study in the formulation of curcuminoid with essential oil of turmeric with 45% Ar-turmerone in 12:1 and 10:1 ratios. The results are summarized in Table 9 (FIG. 6). Treatment with formulation of curcuminoid with essential oil of turmeric with 45% Ar-turmerone in 12:1 ratio group showed decreased C reactive protein from 12 mg/L at baseline to 5.3 mg/L at the end of treatment and formulation of curcuminoid with essential oil of turmeric with 45% Ar-turmerone in 10:1 ratio showed decreased C reactive protein from 12 mg/L at baseline to 5.7 mg/L at the end of treatment. The results are summarized in Table 10. Treatment with formulation of curcuminoid with essential oil of turmeric with 45% Ar-turmerone in 12:1 ratio group showed decrease in Rheumatoid Arthritis factor from 23 IU/L at baseline to 13 IU/L at the end of treatment. Formulation of curcuminoid with essential oil of turmeric with 45% Ar-turmerone in 10:1 ratio showed decrease in Rheumatoid Arthritis factor from 24 IU/L at baseline to 15 IU/L at the end of treatment. The results are summarized in Table 11. The study shows that formulation of curcuminoid with essential oil of turmeric with 45% Ar-turmerone in 10:1 and 12:1 ratios can provide significant improvement in treatment efficacy in active RA. All the patients who were given raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio or curcuminoids 95% capsules showed no significant improvement with treatment and some of the patients even showed worsening of their symptoms with time even with treatment.

TABLE 7

Treatment efficacy results—Disease Activity Score

| Group | | Baseline | End of Treatment | % Change |
|---|---|---|---|---|
| Raw turmeric | Mean | 6 | 6.5 | 8% |
| EOT with 45% Ar-t | Mean | 6.5 | 6.5 | 0 |
| EOT with 10-15% Ar-t | Mean | 6.5 | 7 | 7% |
| C + E with 45% Ar-t in 1:10 ratio | Mean | 7 | 7.5 | 6.6% |
| C + E with 45% Ar-t in 1:1 ratio | Mean | 7.5 | 7.5 | 0 |
| C 24% + E with 45% Ar-t in 10:1 ratio | Mean | 7 | 7 | 0 |
| C + E with 10-15% Ar-t in 10:1 ratio | Mean | 6 | 6 | 0 |
| C + E with 45% Ar-t in 10:1 ratio | Mean | 6.5 | 3.5 | 46% |
| Curcuminoids 95% | Mean | 6.5 | 6 | 8% |
| C + E with 45% Ar-t in 12:1 ratio | Mean | 6.5 | 3 | 54% |

TABLE 8

Treatment efficacy results—VAS

| Group | | Baseline (mm) | End of Treatment (mm) | % Change |
|---|---|---|---|---|
| Raw turmeric | Mean | 80 | 78 | 2.5% |
| EOT with 45% Ar-t | Mean | 75 | 77 | 2.6% |
| EOT with 10-15% Ar-t | Mean | 77 | 78 | 1.3% |
| C + E with 45% Ar-t in 1:10 ratio | Mean | 79 | 77 | 2.5% |
| C + E with 45% Ar-t in 1:1 ratio | Mean | 78 | 76 | 2.6% |
| C 24% + E with 45% Ar-t in 10:1 ratio | Mean | 76 | 74 | 2.6% |
| C + E with 10-15% Ar-t in 10:1 ratio | Mean | 75 | 71 | 5.3% |
| C + E with 45% Ar-t in 10:1 nitio | Mean | 79 | 27.5 | 65% |
| Curcuminoids 95% | Mean | 77 | 70 | 9% |
| C + E with 45% Ar-t in 12:1 ratio | Mean | 78 | 24 | 69% |

TABLE 10

Treatment efficacy results—CRP

| Group | | Baseline (mg/L) | End of Treatment (mg/L) | % Change |
|---|---|---|---|---|
| Raw turmeric | Mean | 13 | 13 | 0 |
| EOT with 45% Ar-t | Mean | 11 | 11.5 | 4% |
| EOT with 10-15% Ar-t | Mean | 12.5 | 13.5 | 7% |
| C + E with 45% Ar-t in 1:10 ratio | Mean | 12 | 12.5 | 4% |
| C + E with 45% Ar-t in 1:1 ratio | Mean | 13 | 13 | 0 |
| C 24% + E with 45% Ar-t in 10:1 ratio | Mean | 12 | 12 | 0 |
| C + E with 10-15% Ar-t in 10:1 ratio | Mean | 11.5 | 11.5 | 0 |
| C + E with 45% Ar-t in 10:1 ratio | Mean | 12 | 5.7 | 53% |
| Curcuminoids 95% | Mean | 11.5 | 11.4 | 1% |
| C + E with 45% Ar-t in 12:1 ratio | Mean | 12 | 5.3 | 56% |

TABLE 11

Treatment efficacy results—Rheumatoid Arthritis Factor

| Group | | Baseline (IU/L) | End of Treatment (IU/L) | % Change |
|---|---|---|---|---|
| Raw turmeric | Mean | 23 | 25 | 8% |
| EOT with 45% Ar-t | Mean | 26 | 28 | 7% |
| EOT with 10-15% Ar-t | Mean | 25 | 26 | 3.8% |
| C + E with 45% Ar-t in 1:10 ratio | Mean | 23 | 24 | 4% |
| C + E with 45% Ar-t in 1:1 ratio | Mean | 22 | 22 | 0 |
| C 24% + E with 45% Ar-t in 10:1 ratio | Mean | 21 | 21 | 0 |
| C + E with 10-15% Ar-t in 10:1 ratio | Mean | 24 | 24 | 0 |
| C + E with 45% Ar-t in 10:1 ratio | Mean | 24 | 15 | 38% |
| Curcuminoids 95% | Mean | 22 | 24 | 9% |
| C + E with 45% Ar-t in 12:1 ratio | Mean | 22 | 13 | 39% |

Example 21

Human Clinical Study of Different Turmeric Extracts in Patients with Osteo Arthritis In a human clinical trial to determine the effectiveness of formulation of curcuminoid with essential oil of turmeric with 45% Ar-turmerone in 10:1 ratio in relieving symptoms and clinical conditions of osteoarthritic patients compared with raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio, formulation of curcuminoid with essential oil of turmeric with 45% Ar-turmerone in 12:1 ratio and curcuminoids 95% capsules, patients of either sex diagnosed to have osteoarthritis according to ACR criteria were selected for the study. The patients were divided into nine groups of 5 patients each.

Gr 1: Oral administration of raw turmeric powder 500 mg capsules, prepared as described in Example 18, in twice daily dosage Gr 2: Oral administration of essential oil of turmeric with 45% Ar-turmerone (EOT with 45% Ar-t) 500 mg capsules prepared as described in Example 14, in twice daily dosage.

Gr3: Oral administration of essential oil of turmeric with 10-15% Ar-turmerone (EOT with 10-15% Ar-t) 500 mg capsules prepared as described in Example 15, in twice daily dosage.

Gr4: Oral administration of curcuminoid with essential oil of turmeric with 45% Ar-turmerone in 1:10 ratio (C+E with 45% Ar-t in 1:10 ratio), 500 mg capsules prepared as described in Example 11, in twice daily dosage.

Gr5: Oral administration of curcuminoid with essential oil of turmeric with 45% Ar-turmerone in 1:1 ratio (C+E with 45% Ar-t in 1:1 ratio), 500 mg capsules prepared as described in Example 12, in twice daily dosage.

Gr6: Subjects receiving curcuminoid 24% with essential oil of turmeric with 45% Ar-turmerone in 10:1 ratio (C 24%+E with 45% Ar-t in 10:1 ratio), 500 mg capsules prepared as described in Example 17 twice daily Gr7: Oral administration of curcuminoid with essential oil of turmeric with 10-15% Ar-turmerone in 10:1 ratio (C+E with 10-15% Ar-t in 10:1 ratio), 500 mg capsules prepared as described in Example 13, in twice daily dosage.

Gr8: Oral administration of formulation of curcuminoid with essential oil of turmeric with 45% Ar-turmerone in 10:1 ratio (C+E with 45% Ar-t in 10:1 ratio), 500 mg capsule prepared as described in Example 10, in twice daily dosage Gr 9: Oral administration of curcuminoids 95% 500 mg capsule prepared as described in Example 16, in twice daily dosage.

Gr10: Oral administration of formulation of curcuminoid with essential oil of turmeric with 45% Ar-turmerone in 12:1 ratio (C+E with 45% Ar-t in 12:1 ratio), 500 mg capsule prepared as described in Example 19, in twice daily dosage Each patient was given treatment for 12 weeks. The efficacy of the use of the study drugs over the treatment period was evaluated by symptom scoring and clinical examination. Symptom refers to the complaints expressed by the patient and scored depending on severity. Symptom scoring includes joint pain measurements and walking distance measurements. Joint pain in osteoarthritis is a deep pain localized to the joint and is measured by querying the patient and scoring it as No/mild/moderate/severe during each visit. Results of this analysis for the eight treatment groups are presented in Table 12 (FIG. 7). Walking distance refers to the maximum distance a person is able to walk at a stretch without limiting pain. Walking distance measurements were recorded and are given Table 13 (FIG. 8). Joint line tenderness was elicited by palpating along the joint line and was measured by querying the patient and recording the response as No/mild/moderate/severe and was recorded and results are presented in Table 14 (FIG. 9).

Crepitus (crackling or grating feeling or sound in joints) is elicited by palpating the joint on movement and scoring it as No/Mild/Moderate/Severe. Range of movement of the knee is measured for flexion/extension movement and the normal range is from 0 to 135 degrees (0 being neutral position and increasing flexion of the joint is normally up to 135 degrees). It is measured using a Goniometer and is measured by asking the patient to flex the joint to the maximum extent possible and the maximum value was recorded.

The results showed that the % response of patients taking formulation of curcuminoid with essential oil of turmeric with 45% Ar-turmerone in 10:1 and 12:1 ratios were significantly better than patients taking raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio and curcuminoids 95% capsules. At the beginning of study all patients had joint pain and after treatment with formulation of curcuminoid with essential oil of turmeric with 45% Ar-turmerone in 12:1 ratio, 19% patients did not have any joint pain. The percentage of patients with moderate joint pain decreased from 80% at baseline to 29% at the end of treatment and majority of the patients (52%) had only mild pain at the end of 3 months of treatment in patients given formulation of curcuminoid with essential oil of turmeric with 45% Ar-turmerone in 12:1 ratio. Before the treatment 7% of patients had severe joint pain and after treatment none of the patients given formulation of curcuminoid with essential oil of turmeric with 45% Ar-turmerone in 12:1 ratio had severe joint pain.

At the beginning of study all patients had joint pain and after treatment with formulation of curcuminoid with essential oil of turmeric with 45% Ar-turmerone in 10:1 ratio, 17% patients did not have any joint pain. The percentage of patients with moderate joint pain decreased from 78% at baseline to 30% at the end of treatment and majority of the patients (53%) had only mild pain at the end of 3 months of treatment in patients given formulation of curcuminoid with essential oil of turmeric with 45% Ar-turmerone in 10:1 ratio. Before the treatment 7% of patients had severe joint pain and after treatment none of the patients given formulation of curcuminoid with essential oil of turmeric with 45% Ar-turmerone in 10:1 ratio had severe joint pain.

Before the treatment 87% of patients given formulation of curcuminoid with essential oil of turmeric with 45% Ar-turmerone in 12:1 ratio had joint line tenderness and after treatment 52% of patients no longer had pain and the remaining 48% patients showed improvement and none of the patient's condition worsened or remained same without change.

Before the treatment 86% of patients given formulation of curcuminoid with essential oil of turmeric with 45% Ar-turmerone in 10:1 ratio had joint line tenderness and after treatment 50% of patients no longer had pain and the remaining 50% patients showed improvement and none of the patient's condition worsened or remained same without change.

Before the treatment with formulation of curcuminoid with essential oil of turmeric with 45% Ar-turmerone in 12:1 ratio 8% of patients could not walk even up to 100 meters. And after the treatment 75% of patients could walk over 1000 meters and 22% could walk 500-1000 meters.

Before the treatment with formulation of curcuminoid with essential oil of turmeric with 45% Ar-turmerone in 10:1 ratio 7% of patients could not walk even up to 100 meters. And after the treatment 72% of patients could walk over 1000 meters and the remaining 28% could walk 500-1000 meters.

The safety of the test drug was evaluated by measuring vital signs (systolic and diastolic blood pressure, pulse rate, respiratory rate), haemogram measurement (Hb, TC, DC, ESR), liver function tests (SGOT, SGPT, SAP, bilirubin), renal function tests (blood urea, serum creatinine). None of these parameters were adversely modified by the study drugs. There were also no adverse events reported in the study.

In conclusion, formulation of curcuminoid with essential oil of turmeric with 45% Ar-turmerone in 10:1 and 12:1 ratios were significantly effective compared to raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio and curcuminoids 95% capsules in relieving symptoms and clinical conditions of osteoarthritic patients when given over a period of 3 months. There was significant improvement in pain scores, walking distance, joint line tenderness, crepitus, range of movement of the knee and joint swelling measurements in osteoarthritic patients receiving formulation of curcuminoid with essential oil of turmeric with 45% Ar-turmerone in 10:1 and 12:1 ratios for 3 months compared to patients receiving raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio and curcuminoids 95% capsules in the similar dosage. The study drugs were well tolerated and no dose-related toxicity was found.

Example 22

Human Clinical Study in Patients with Alzheimers Disease

A double-blind, placebo-controlled, pilot clinical trial formulation of curcuminoid with essential oil of turmeric with 45% Ar-turmerone in 10:1 and 12:1 ratio capsules compared with raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio and curcuminoids 95% capsules was done in patients with progressive decline in memory or cognitive function and diagnosed with probable or possible Alzheimer's disease (AD). Patients were randomized to 10 groups to receive 3.0 grams of each study drug capsules twice daily for 12 months.

Parameters measured at baseline and end of study include plasma isoprostanes, Vit E, Aβ and clinical assessment with Mini-Mental State Examination Scores (MMSE). Isoprostanes are the products of non-enzymatic oxidation of arachidonic acid and so this, along with the antioxidant Vit E levels is indicative of the level of oxidative stress. Aβ are a 39-43 amino acid peptide fragment derived from the β-amyloid precursor protein (APP) and are the predominant component of the neuritic plaques, an invariant pathological hallmark of AD. Aggregated forms of Aβ are believed to be the real culprits of the disease. Mini-Mental State Examination Scores (MMSE) is a measure of cognitive function. The pharmacokinetics of curcumin from the ingested drugs and adverse events, if any, associated with the drug were also recorded.

Serum Aβ levels was significantly higher in formulation of curcuminoid with essential oil of turmeric with 45% Ar-turmerone in 10:1 and 12:1 ratio capsules compared to results following administration of raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio and curcuminoids 95% capsules, reflecting the increased ability of formulation of curcuminoid with essential oil of turmeric with 45% Ar-turmerone in 10:1 and 12:1 ratio capsules to disaggregate AΔ deposits in the brain. The MMSE scores of patients given formulation of curcuminoid with essential oil of turmeric with 45% Ar-turmerone in 10:1 ratio capsules increased significantly from baseline value at $16/30$ to $23/30$ at the end of the study. The MMSE scores of patients given formulation of curcuminoid with essential oil of turmeric with 45% Ar-turmerone in 12:1 ratio capsules increased significantly from baseline value at $17/30$ to $25/30$ at the end of the study and in patients given raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio and curcuminoids 95% capsules there was a marginal deterioration in the MMSE score (Table 15). Isoprostanes are products of non-enzymatic oxidation of arachidonic acid and are indicative of oxidative stress. Plasma isoprostane levels were significantly lowered between baseline and at 12 months in patients taking formulation of curcuminoid with essential oil of turmeric with 45% Ar-turmerone in 10:1 and 12:1 ratios. Vitamin E levels increased in the formulation of curcuminoid with essential oil of turmeric with 45% Ar-turmerone in 10:1 and 12:1 ratio groups from baseline to end of treatment. (Table 16). The curcumin level in patients taking formulation of curcuminoid with essential oil of turmeric with 45% Ar-turmerone in 10:1 ratio (baseline at 12 to 653 at the end of treatment period) was 15 times higher than patients taking curcuminoids 95% capsules (baseline at 13 to 42 at the end of treatment) (Table 17). The curcumin level in patients taking formulation of curcuminoid with essential oil of turmeric with 45% Ar-turmerone in 12:1 ratio (baseline at 14 to 875 at the end of treatment period) was 20 times higher than patients taking curcuminoids 95% capsules (baseline at 13 to 42 at the end of treatment) (Table 17). In patients taking raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio and curcuminoids 95% capsules there was no decrease noticed in the plasma isoprostane levels and Vitamin E levels remained more or less the same in all the groups except in patients taking formulation of curcuminoid with essential oil of turmeric with 45% Ar-turmerone in 10:1 and 12:1 ratios.

This study thus reveals that the formulation of curcuminoid with essential oil of turmeric with 45% Ar-turmerone in 10:1 and 12:1 ratio capsules confer greater clinical benefits as observed by significant increase in the MMSE score, increase in Vit E levels, high levels of serum Aβ levels, and lowered plasma isoprostane levels in patients consuming formulation of curcuminoid with essential oil of turmeric with 45% Ar-turmerone in 10:1 and 12:1 ratio capsules compared with patients consuming raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio and curcuminoid 95% capsules for 12 months.

TABLE 15

MMSE levels of patients in each group over 12 months

| Groups | | Baseline 0 month | Study End 12 months |
|---|---|---|---|
| Raw turmeric | MMSE | 16/30 | 14/30 |
| EOT with 45% Ar-t | MMSE | 15/30 | 14/30 |
| EOT with 10-15% Ar-t | MMSE | 18/30 | 16/30 |
| C + E with 45% Ar-t in 1:10 ratio | MMSE | 16/30 | 15/30 |
| C + E with 45% Ar-t in 1:1 ratio | MMSE | 18/30 | 17/30 |
| C 24% + E with 45% Ar-t in 10:1 ratio | MMSE | 16/30 | 16/30 |
| C + E with 10-15% Ar-t in 10:1 ratio | MMSE | 17/30 | 17/30 |
| C + E with 45% Ar-t in 10:1 ratio | MMSE | 16/30 | 23/30 |
| Curcuminoids 95% | MMSE | 17/30 | 16/30 |
| C + E with 45% Ar-t in 12:1 ratio | MMSE | 17/30 | 25/30 |

TABLE 16

Vitamin E levels of patients in each group over 12 months

| Groups | | Baseline 0 month | Study End 12 months |
|---|---|---|---|
| Raw turmeric | Vit E in mg % | 0.4 | 0.4 |
| EOT with 45% Ar-t | Vit. E in mg % | 0.3 | 0.3 |
| EOT with 10-15% Ar-t | Vit E in mg % | 0.3 | 0.3 |
| C + E with 45% Ar-t in 1:10 ratio | Vit. E in mg % | 0.4 | 0.4 |
| C + E with 45% Ar-t in 1:1 ratio | Vit. E in mg % | 0.3 | 0.3 |
| C 24% + E with 45% Ar-t in 10:1 ratio | Vit E in mg % | 0.4 | 0.4 |
| C + E with 10-15% Ar-t in 10:1 ratio | Vit E in mg % | 0.3 | 0.4 |
| C + E with 45% Ar-t in 10:1 ratio | Vit E in mg % | 0.30 | 2.1 |
| Curcuminoids 95% | Vit E in mg % | 0.4 | 0.4 |

TABLE 16-continued

Vitamin E levels of patients in each group over 12 months

| Groups | | Baseline 0 month | Study End 12 months |
|---|---|---|---|
| C + E with 45% Ar-t in 12:1 ratio | Vit E in mg % | 0.3 | 2.8 |

TABLE 17

Plasma level of curcumin in patients in each group over 12 months

| Groups | | Baseline 0 month | Study End 12 months |
|---|---|---|---|
| Raw tumeric | Curcumin in nMol/L | 11 | 20 |
| EOT with 45% Ar-t | Curcumin in nMol/L | 9 | 11 |
| EOT with 10-15% Ar-t | Curcumin in nMol/L | 12 | 11 |
| C + E with 45% Ar-t in 1:10 ratio | Curcumin in nMol/L | 10 | 13 |
| C + E with 45% Ar-t in 1:1 ratio | Curcumin in nMol/L | 21 | 145 |
| C 24% + E with 45% Ar-t in 10:1 ratio | Curcumin in nMol/L | 14 | 28 |
| C + E with 10-15% Ar-t in 10:1 ratio | Curcumin in nMol/L | 15 | 82 |
| C + E with 45% Ar-t in 10:1 ratio | Curcumin in nMol/L | 12 | 653 |
| Curcuminoids 95% | Curcumin in nMol/L | 13 | 42 |
| C + E with 45% Ar-t in 12:1 ratio | Curcumin in nMol/L | 14 | 875 |

Example 23

Human Clinical Study of Patients with Depression

In a randomized, double blind, active control, parallel group study, formulation of curcuminoid with essential oil of turmeric with 45% Ar-turmerone in 10:1 and 12:1 ratios were studied against raw turmeric powder, essential oil of turmeric with 45% Ar-turmerone, essential oil of turmeric with 10-15% Ar-turmerone, curcuminoid with essential oil of turmeric with 45% Ar-turmerone in 1:10 ratio, curcuminoid with essential oil of turmeric with 45% Ar-turmerone in 1:1 ratio, curcuminoid 24% with essential oil of turmeric with 45% Ar-turmerone in 10:1 ratio, curcuminoid with essential oil of turmeric with 10-15% Ar-turmerone in 10:1 ratio and curcuminoid 95% capsules in patients with depression to compare the efficacy and tolerability of the eight formulations. Patients with a Score greater than 7 but less than 24 on the 17-item Hamilton Depression (HAM-D) Scale and assessed by Structured Clinical Interview or DSM-IV Axis 1 Disorders without any concurrent treatment were selected for the study. 50 patients selected were randomized into 10 groups and were given treatment for 8 weeks.

Gr 1: raw turmeric powder 500 mg capsules prepared as described in Example 18 twice daily Gr 2: essential oil of turmeric with 45% Ar-turmerone (EOT with 45% Ar-t) 500 mg capsules prepared as described in Example 14 twice daily Gr3: essential oil of turmeric with 10-15% Ar-turmerone (EOT with 10-15% Ar-t) 500 mg capsules prepared as described in Example 15 twice daily Gr4: curcuminoid with essential oil of turmeric with 45% Ar-turmerone in 1:10 ratio (C+E with 45% Ar-t in 1:10 ratio), 500 mg capsules prepared as described in Example 11 twice daily Gr5: curcuminoid with essential oil of turmeric with 45% Ar-turmerone in 1:1 ratio (C+E with 45% Ar-t in 1:1 ratio), 500 mg capsules prepared as described in Example 12 twice daily.

Gr6: Subjects receiving curcuminoid 24% with essential oil of turmeric with 45% Ar-turmerone in 10:1 ratio (C 24%+E with 45% Ar-t in 10:1 ratio), 500 mg capsules prepared as described in Example 17 twice daily.

Gr7: curcuminoid with essential oil of turmeric with 10-15% Ar-turmerone in 10:1 ratio (C+E with 10-15% Ar-t in 10:1 ratio), 500 mg capsules prepared as described in Example 13 twice daily.

Gr 8: curcuminoids 95% (500 mg) capsules prepared as described in example 16 twice daily.

Gr 9: Formulation of curcuminoid with essential oil of turmeric with 45% Ar-turmerone in 10:1 ratio (C+E with 45% Ar-t in 10:1 ratio) (500 mg) capsules prepared as described in Example 10 twice daily.

Gr 10: Formulation of curcuminoid with essential oil of turmeric with 45% Ar-turmerone in 12:1 ratio (C+E with 45% Ar-t in 12:1 ratio) (500 mg) capsules prepared as described in Example 19 twice daily.

Efficacy was evaluated by using 17 point—Hamilton depression scale and clinical global impression by Global Severity (CGI-S) and Global change (CGI-I) scales. Tolerability of the drugs was assessed clinically and by biochemical parameters like SGOT, SGPT, Urea and Creatinine (measured at the start and at the end of study).

Results: The proportion of responders as measured by the HAM-D17 scale was significantly (97%) higher in the formulation of curcuminoid with essential oil of turmeric with 45% Ar-turmerone in 12:1 ratio group than other groups (Table: 18). The proportion of responders as measured by the RAM-D17 scale was significantly (93%) higher in the formulation of curcuminoid with essential oil of turmeric with 45% Ar-turmerone in 10:1 ratio group than other groups (Table: 18). The change in HAM-D17 scores at the end of 8 weeks from baseline at 20 to 7 at the end of treatment was higher for formulation of curcuminoid with essential oil of turmeric with 45% Ar-turmerone in 12:1 ratio group (65%) than other groups (Table: 19). The change in HAM-D17 scores at the end of 8 weeks from baseline at 21 to 10 at the end of treatment was also higher for formulation of curcuminoid with essential oil of turmeric with 45% Ar-turmerone in 10:1 ratio group (52%) than other groups (Table: 19). In Clinical Global Impression assessment scale, the formulation of curcuminoid with essential oil of turmeric with 45% Ar-turmerone in 12:1 ratio group showed a decrease in CGI-S score from baseline at 4 to 1 at the end of treatment. That is 75% improvement in CGI-S (Table; 20). In Clinical Global Impression assessment scale, the formulation of curcuminoid with essential oil of turmeric with 45% Ar-turmerone in 10:1 ratio group showed a decrease in CGI-S score from baseline at 5 to 2 at the end of treatment. That is 60% improvement in CGI-S (Table: 20). Formulation of curcuminoid with essential oil of turmeric with 45% Ar-turmerone in 12:1 ratio group showed a decrease in CGI-I score from baseline 5 to 2 at the end of treatment. That is 60% improvement in CGI-1 scale (Table: 21). Formulation of curcuminoid with essential oil of turmeric with 45% Ar-turmerone in 10:1 ratio group showed a decrease in CGI-1 score from baseline 4 to 2 at the end of treatment. That is 50% improvement in CGI-1 scale (Table: 21). Whereas the other groups showed no change at all at the end of 8 weeks of treatment. Overall the study medications were well tolerated and there was no significant difference in vital signs, physical examination, laboratory tests and electrocardiogram from baseline and had 'excellent' tolerability.

TABLE 18

Proportion of responders in each group over 2 months

| | | |
|---|---|---|
| Raw turmeric | % response rate on HAM-D17 scale | 6% |
| EOT with 45% Ar-t | % response rate on HAM-D17 scale | 4% |
| EOT with 10-15% Ar-t | % response rate on HAM-D17 scale | 4% |
| C + E with 45% Ar-t in 1:10 ratio | %, response rate on HAM-D17 scale | 7% |
| C + E with 45% Ar-t in 1:1 ratio | % response rate on HAM-D17 scale | 9% |
| C 24% + E with 45% Ar-t in 10:1 ratio | % response rate on HAM-D17 scale | 8% |
| C + E with 10-15% Ar-t in 10:1 ratio | % response rate on HAM-D17 scale | 12% |
| C + E with 45% Ar-t in 10:1 ratio | % response rate on HAM-D17 scale | 93% |
| Curcuminoids 95% | % response rate on HAM-D17 scale | 10% |
| C + E with 45% Ar-t in 12:1 ratio | % response rate on HAM-D17 scale | 97% |

TABLE 19

Hamilton Depression Scoring Scale—17 point scale in patients in each group over 2 months

| Groups | | Baseline 0 month | Study End 2 months |
|---|---|---|---|
| Raw turmeric | HAM-D17 scale | 20 | 19 |
| EOT with 45% Ar-t | HAM-D17 scale | 19 | 19 |
| EOT with 10-15% Ar-t | HAM-D17 scale | 22 | 22 |
| C + E with 45% Ar-t in 1:10 ratio | HAM-D17 scale | 18 | 18 |
| C + E with 45% Ar-t in 1:1 ratio | HAM-D17 scale | 20 | 19 |
| C 24% + E with 45% Ar-t in 1:10 ratio | HAM-D17 scale | 19 | 19 |
| C + E with 10-15% Ar-t in 10:1 ratio | HAM-D17 scale | 19 | 16 |
| C + E with 45% Ar-t in 10:1 ratio | HAM-D17 scale | 21 | 10 |
| Curcuminoids 95% | HAM-D17 scale | 19 | 17 |
| C + E with 45% Ar-t in 12:1 ratio | HAM-D17 scale | 20 | 7 |

TABLE 20

Clinical Global Impression—Severity Scale in patients in each group over 2 months

| Groups | | Baseline 0 month | Study End 12 months |
|---|---|---|---|
| Raw turmeric | CGI-S score | 5 | 5 |
| EOT with 45% Ar-t | CGI-S score | 4 | 4 |
| EOT with 10-15% Ar-t | CGI-S score | 4 | 4 |
| C + E with 45% Ar-t in 1:10 ratio | CGI-S score | 5 | 5 |
| C + E with 45% Ar-t in 1:1 ratio | CGI-S score | 4 | 4 |

TABLE 20-continued

Clinical Global Impression—Severity Scale in
patients in each group over 2 months

| Groups | | Baseline 0 month | Study End 12 months |
|---|---|---|---|
| C 24% + E with 45% Ar-t in 10:1 ratio | CGI-S score | 4 | 4 |
| C + E with 10-15% Ar-t in 10:1 ratio | CGI-S score | 5 | 5 |
| C + E with 45% Ar-t in 10:1 ratio | CGI-S score | 5 | 2 |
| Curcuminoids 95% | CGI-S score | 5 | 5 |
| C + E with 45% Ar-t in 12:1 ratio | CGI-S score | 4 | 1 |

TABLE 21

Clinical Global Impression—Improvement/Change
Scale in patients in each group over 2 months

| Groups | | Baseline 0 month | Study End 12 months |
|---|---|---|---|
| Raw turmeric | CGI-I score | 4 | 4 |
| EOT with 45% Ar-t | CGI-I score | 4 | 4 |
| EOT with 10-15% Ar-t | CGI-I score | 4 | 4 |
| C + E with 45% Ar-t in 1:10 ratio | CGI-I score | 5 | 5 |
| C + E with 45% Ar-t in 1:1 ratio | CGI-I score | 4 | 4 |
| C 24% + E with 45% Ar-t in 10:1 ratio | CGI-I score | 4 | 4 |
| C + E with 10-15% Ar-t in 10:1 ratio | CGI-I score | 5 | 5 |
| C + E with 45% Ar-t in 10:1 ratio | CGI-I score | 4 | 2 |
| Curcuminoids 95% | CGI-I score | 4 | 4 |
| C + E with 45% Ar-t 12:1 ratio | CGI-I score | 5 | 2 |

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

REFERENCES

1. Kelloff, G. I., et al, J. Cell Biochem., 1996, 265:54-71.
2. Rao, C. V. et al, Cancer Res., 1995, 55:259-66.
3. Kawamori, T. et al, Cancer Res., 1999, 59:597-601.
4. Mahmood. N. N. et al, Carcinogenesis, 2000, 31:921-27.
5. Subramanian, M. et al, Mutat. Res., 1994, 311:249-55.
6. Tonnesen, H. H. et al, Int. J. Pharm., 1992, 87:79-87.
7. Reddy, A. C. P. et al, Mol. Cell Biochem., 1994, 137:1-8.
8. Donatus, I. A., Biochem. Pharmacol., 1990, 39:1869-75.
9. Sharma. S. C. et al, Biochem. Pharmacol., 1972, 21:1210-14.
10. Liu, J. V. et al, Carcinogenesis, 1993, 14:857-61.
11. Huang, T. S. et al, Proc. Natl. Acad. Sci., 1991, 88:5292-96.
12. Huang, M-T. et al, In L. W. Battenberg (ed.) Cancer Chemo prevention, CRC Press, Boca Raton, 1992, pp 375-91.
13. Huang. M. T. et al, Cancer Res., 1991, 51:813-19.
14. Zhang, F. et al, Carcinogenesis, 1999, 20:445-51.
15. Plummer, S. et al, Oncogene, 1999, 18:6013-20.
16. Funk, C. D. et al, FASEB J., 1991, 5:2304-12.
17. Subbaramiah, K. et al, 1996, Cancer Res., 1996, 56:4424-29.
18. DuBois, R. N. et al. J. Clin. Invest., 1994, 93:493-98.
19. Kelley, D. J. et al, Carcinogenesis, 1997, 18:795-99.
20. Huang, M. T., et al Cancer Res., 1988, 48:5941-46; 1991, 51:813-19.
21. Rao, C. V. et al., Cancer Res., 1995, 55:259-66.
22. Ireson, C. R. et al, Cancer Res., 2001, 41:1058-64.
23. Sharma, R. A. et al, Clin. Cancer Res., 2001, 7:1834-1900.
24. Pan, M. H. et al, Drug Metabol. Dispos., 1999, 27:486-94.
25. Asai, A., et al, Life Sci., 2000, 67:2785-93.
26. Ireson et at, loc. cit.
27. Ireson, C. R. et al, Cancer Epidemiol. Biomark. Prev., 2002, 11:105-11.
28.3 Ravindranath, V. and Chandrasekhara, N., Toxicology, 1981, 20:251-57.
29. Asai et al, loc cit.
30. Ireson, C. R., et al, Cancer Epidemiol. Biomark. Prev., 2002, 11:105-11.
31. Perkins, S. et al, Cancer Epidemiol. Biomark. Prev., 2002, 11:535-40.
32. Limtrakul, P., et at, Cancer Lett., 1997, 116:197-203.
33. Chiang, S. E. et al, Carcinogenesis, 2000, 21:331-35.
34. Inano, H. et al, Carcinogenesis, 2000, 21:1835-41; Int. J. Radiat. Oncol. Biol. Phys., 2002, 52:212-23; ibid, 2002, 53:735-43.
35. Garcea, G. et al, Cancer Epidemiol. Biomark. Prev., 2005, 14:120-25.
36. Shobha et al, Planta Med., 1998, 64:353-56

We claim:

1. A method of treating a central nervous system disorder in a subject in need thereof, the method comprising administering to said subject in need thereof a composition comprising an effective amount of a blend consisting of:
   a.) a curcuminoid mixture consisting of curcumin, demethoxycurcumin, and bisdemethoxycurcumin; and
   b.) a fraction of essential oil of turmeric comprising 45% ar-turmerone,
   wherein the weight ratio of a.) to b.) in the blend is about 1:3 to about 99:1, and
   wherein the central nervous system disorder is depression.

2. The method of claim 1, wherein the weight ratio of a.) to b.) is about 10:1.

3. The method of claim 1, wherein the weight ratio of a.) to b.) is about 12:1.

4. The method of claim 1, wherein the effective amount of the blend is about 500 mg.

5. The method of claim 1, wherein a.) is in an amount of about 454.55 mg.

6. The method of claim 1, wherein b.) is in an amount of about 45.45 mg.

7. The method of claim 1, wherein a.) is in an amount of about 461.55 mg.

8. The method of claim 1, wherein b.) is in an amount of about 38.5 mg.

9. The method of claim 1, wherein a.) is in an amount of about 454.55 mg, and b.) is in an amount of about 45.45 mg.

10. The method of claim 1, wherein a,) is in an amount of about 461.5 mg, and b.) is in an amount of about 38.5 mg.

11. The method of claim 1, wherein the composition is a gelatin capsule.

12. The method of claim 11, wherein the gelatin capsule comprises 500 mg of the blend.

13. The method of claim 12, wherein the gelatin capsule is administered twice daily for 8 weeks.

14. The method of claim 1, wherein administering the composition improves the response rate of the subject on a Hamilton Depression rate scale after two months.

15. The method of claim 14, wherein the response rate of the subject on the Hamilton Depression rate scale decreases from about 21 to about 7 two months after administering the composition.

16. The method of claim 14, wherein the response rate of the subject on the Hamilton Depression rate scale improves by about 65% after administering the composition.

17. The method of claim 14, wherein the response rate of the subject on the Hamilton Depression rate scale improves by about 52% after administering the composition.

18. The method of claim 1, wherein administering the composition improves the Clinical Global Severity score (CGI-S) of the subject.

19. The method of claim 18, wherein the Clinical Global Severity score (CGI-S) decreases from about 5 to about 1.

20. The method of claim 18, wherein the Clinical Global Severity score (CGI-S) improves by about 75%.

21. The method of claim 18, wherein the Clinical Global Severity score (CGI-S) improves by about 60%.

22. The method of claim 18, wherein administering the composition improves the Global Change scale (CGI-I) score of the subject.

23. The method of claim 22, wherein the Global Change scale (CGI-I) score decreases from about 5 to about 2 after administering the composition to the subject.

24. The method of claim 22, wherein the Global Change scale (CGI-I) score improves about 60% after administering the composition to the subject.

25. The method of claim 22, wherein the Global Change scale (CGI-I) score improves about 50% after administering the composition to the subject.

26. The method of claim 1, wherein the blend is prepared by the method comprising:
 suspending a.) in water to form a suspension;
 adding b.) to the suspension to form a mixture;
 homogenizing the mixture to obtain a slurry; and
 drying the slurry under heat and vacuum to form the blend.

* * * * *